US012674159B2

(12) United States Patent

Jung et al.

(10) Patent No.: US 12,674,159 B2

(45) Date of Patent: Jul. 7, 2026

(54) SELF-PRIMING AND REPLICATING HAIRPIN ADAPTOR FOR CONSTRUCTING NGS LIBRARY, AND METHOD FOR CONSTRUCTING NGS LIBRARY USING SAME

(71) Applicant: Korea University Research and Business Foundation, Seoul (KR)

(72) Inventors: Cheul Hee Jung, Seoul (KR); Seo Young Kim, Incheon (KR); Jun Y Shin, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 75 days.

(21) Appl. No.: 17/769,636

(22) PCT Filed: Sep. 23, 2020

(86) PCT No.: PCT/KR2020/012904

§ 371 (c)(1),
(2) Date: Apr. 15, 2022

(87) PCT Pub. No.: WO2021/075750

PCT Pub. Date: Apr. 22, 2021

(65) Prior Publication Data

US 2024/0132876 A1    Apr. 25, 2024
US 2024/0229018 A9    Jul. 11, 2024

(30) Foreign Application Priority Data

Oct. 18, 2019    (KR) ........................ 10-2019-0129979

(51) Int. Cl.
*C12N 15/10*        (2006.01)

(52) U.S. Cl.
CPC ................................ *C12N 15/1093* (2013.01)

(58) Field of Classification Search
CPC .................................................. C12N 15/1093
(Continued)

(56) References Cited

U.S. PATENT DOCUMENTS

2012/0083017 A1    4/2012  Mikawa

FOREIGN PATENT DOCUMENTS

JP        2018-530536 A    10/2018
JP        2019-526267 A    9/2019
(Continued)

OTHER PUBLICATIONS

Park, Daechan, et al., "Selection of self-priming molecular replicators", Nucleic Acids Research, Jan. 30, 2019, pp. 2169-2176, vol. 47, No. 5.
(Continued)

*Primary Examiner* — Aaron A Priest
*Assistant Examiner* — Randi Lynn Beil
(74) *Attorney, Agent, or Firm* — Sughrue Mion, PLLC

(57) ABSTRACT

The present invention pertains to: a self-priming and replicating hairpin adaptor for constructing an NGS (next generation sequencing) library; and a method for constructing an NGS library using the same. Specifically, the present invention pertains to: a self-priming and replicating hairpin adaptor for constructing an NGS library, the adaptor containing a long single-stranded first oligonucleotide that comprises a nucleotide sequence of SEQ ID NO: 4 and has a hairpin structure, and a short single-stranded second oligonucleotide that comprises a nucleotide sequence of SEQ ID NO: 5; a method for constructing an NGS library using said adaptor; and an NGS library construction kit including said adaptor.

10 Claims, 12 Drawing Sheets

Specification includes a Sequence Listing.

(58) Field of Classification Search
USPC ........................................................ 506/26
See application file for complete search history.

(56)                    References Cited

FOREIGN PATENT DOCUMENTS

KR          10-1651817  B1        8/2016
WO          2017/202389  A1      11/2017

OTHER PUBLICATIONS

International Search Report for PCT/KR2020/012904 dated Jan. 4,
2021.
Written Opinion for PCT/KR2020/012904 dated Jan. 4, 2021.

Fig. 2

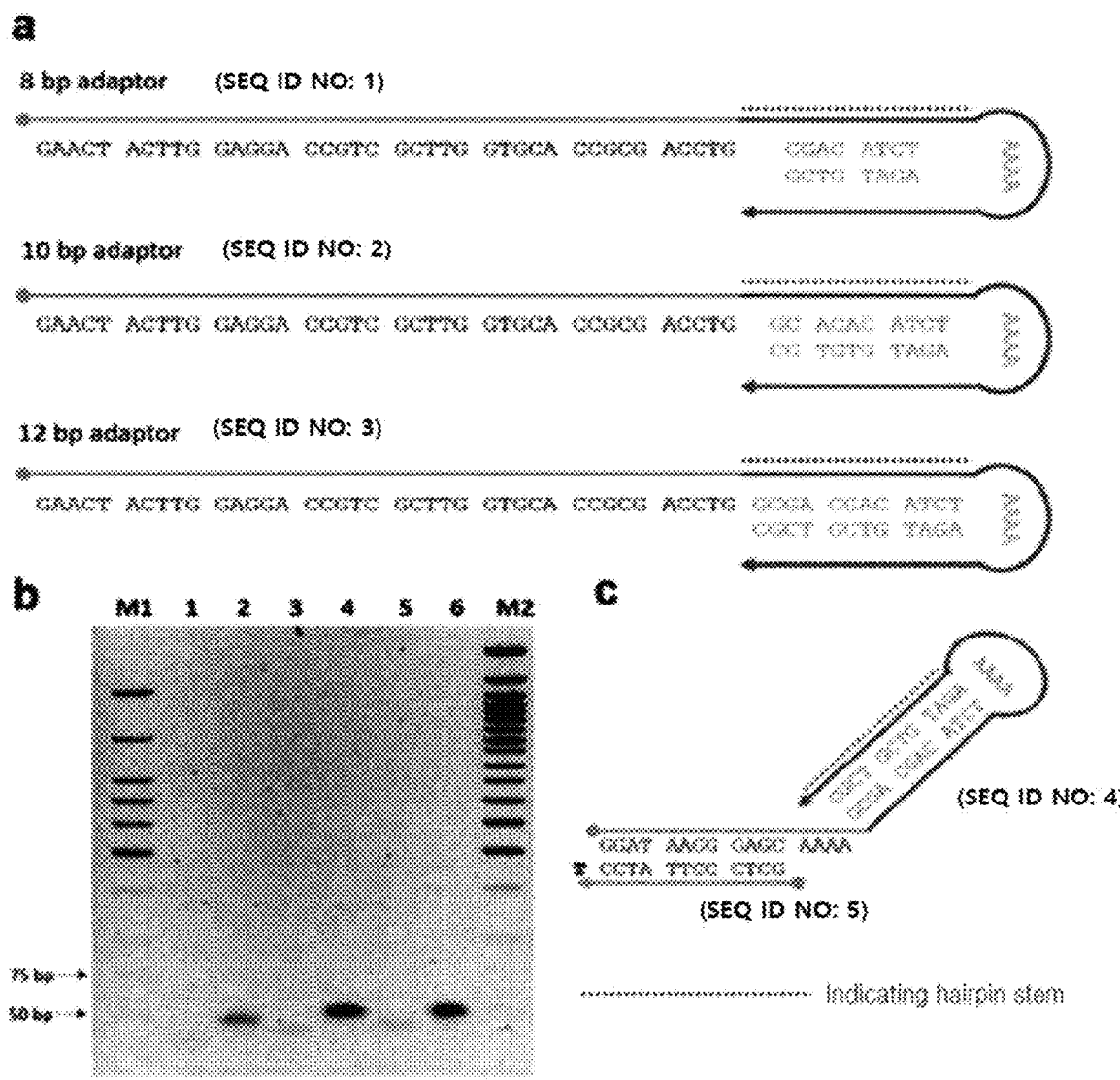

a

8 bp adaptor (SEQ ID NO: 1)

GAACT ACTTG GAGGA CCGTC GCTTG GTGCA CCGCG ACCTG   CCAC ATCT
                                                 GCTG TAGA

10 bp adaptor (SEQ ID NO: 2)

GAACT ACTTG GAGGA CCGTC GCTTG GTGCA CCGCG ACCTG   GG ACAC ATCT
                                                 CC TGTG TAGA

12 bp adaptor (SEQ ID NO: 3)

GAACT ACTTG GAGGA CCGTC GCTTG GTGCA CCGCG ACCTG   GGGA CCAC ATCT
                                                 CCCT GGTG TAGA b    M1  1  2  3  4  5  6  M2

75 bp →
50 bp → c

(SEQ ID NO: 4)

GGAT AACG GAGC AAAA
CCTA TTGC CTCG (SEQ ID NO: 5)

·········· Indicating hairpin stem

SELF-PRIMING AND REPLICATING HAIRPIN ADAPTOR FOR CONSTRUCTING NGS LIBRARY, AND METHOD FOR CONSTRUCTING NGS LIBRARY USING SAME

CROSS REFERENCE TO RELATED APPLICATIONS

This application is a National Stage of International Application No. PCT/KR2020/012904 filed Sep. 23, 2020, claiming priority based on Korean Patent Application No. 10-2019-0129979 filed Oct. 18, 2019, the entire disclosures of which are incorporated herein by reference.

INCORPORATION BY REFERENCE OF SEQUENCE LISTING

The content of the electronically submitted sequence listing, file name: Q274945_substitute sequence listing as filed; size: 3,313 bytes; and date of creation: Oct. 21, 2025, filed herewith, is incorporated herein by reference in its entirety.

BACKGROUND ART

Technical Field

The present invention relates to a self-priming and replicating hairpin adaptor for NGS library preparation and a method for NGS library preparation using the same.

Background Art

Next-generation sequencing (NGS) is massively parallel sequencing technology, and generally refers to high-throughput genome sequencing technology. Such NGS technology has been applied in various fields, including cancer treatment and research, prenatal diagnosis, drug resistance, infectious diseases, and forensics.

Meanwhile, despite the technological advances of NGS, the error rate that occurs during analysis is as high as 0.1 to 1%. The major cause of the error is the polymerase chain reaction (PCR) in the sample preparation process. In addition, the inherent mutation error rate of DNA polymerase and the biased amplification of certain parts of the template DNA may result in incorrect analysis. In addition, when a jackpot error occurs due to the amplification error of the initial template DNA in the first amplification step of PCR, error correction itself is impossible. In addition, there is a problem that a significant error may occur in the sample preparation process even as a result of PCR misincorporation, chimeric PCR products, template switching, and hairpin structure formation.

Furthermore, for heterogeneous samples, there is a problem in that it is difficult to determine whether the observed mutation in actual NGS analysis comes from NGS error or actual mutation, because tumor cells may have different mutations in the same gene due to the heterogeneity of tumors. In addition, in the case of a number of somatic mutations, it is difficult to completely identify these mutations because they are present in small amounts or appear at very low frequencies.

Thus, technologies to solve these problems have been developed. In recent years, a barcode-based or UMI (unique molecular identifier)-based error correction strategy has been developed. This strategy is a method of ligating a barcode, which consists of any nucleotide sequence with a length of about 8 to 14 bp, to a DNA fragment. In this method, the barcode is ligated to the DNA fragment directly via an adaptor or after PCR using primers, followed by tracking and sequencing of individual fragments. However, this method significantly increases the amount of sequencing required per sample and requires an amplification process, and thus the problem of biased amplification or noise generation may still occur.

Another method is Duplex-Sequencing (DupSeq), which is a technique of reducing errors by independently sequencing DNA fragments after ligating different UMIs to the ends of each double strand in the original DNA fragment. Since the two strands are complementary to each other, true mutations are found at the same position in the two strands in the read family. If mutations are detected in one of the two strands but not in the other strand, it can be determined that these mutations are due to damaged DNA or a PCR or sequencing error. However, this method has problems in that it is expensive because the number of reads required per sample is about 100 times larger than that in a common NGS method, and in that PCR amplification bias and the complexity of the workflow increase due to the presence of barcodes.

Another method is Circle-Sequencing (Circle-Seq), in which very short single-stranded DNA is converted into circular DNA and amplified in a circular state to make several linear amplification products, RCA (rolling circle amplification). This method is highly efficient in terms of cost because the replication rate can be maintained uniformly. However, RCA has limitations in terms of length, causes severely biased amplification, and has limitations in detecting rare variants.

In recent years, the O2n-Seq method has been developed and used. The O2n-Seq method is a technology combining the advantages of the barcode and RCA methods, and the O2n-Seq library is a technology that reduces sequencing errors because copies exist in the form of paired ends in one original fragment to form one read family. However, the O2n-Seq method has a problem in that it is difficult to apply to long fragments because the efficiency of making circular DNA is low and the length of the DNA fragment to be analyzed to make circular DNA is limited. In addition, the O2n-Seq method has a problem in that a nick site can generate artifacts as a result of incomplete cleavage and can cause biochemical damage to single-stranded DNA, and thus the performance of polymerase is degraded in the end-repair and A-tailing processes. This may interfere with proper ligation of the adaptor, leading to problems in library preparation. In addition, the uracil-DNA glycosylase (UDG) of USER enzyme, which is used to remove uracil bases, plays a role in releasing the base, but there is a problem in that an abasic site contrary to amplification may be generated.

Therefore, it is necessary to develop a new analysis method that can overcome and solve problems that may occur in these next-generation sequencing methods.

DISCLOSURE

Technical Problem

Accordingly, the present inventors have conducted studies on a method capable of minimizing errors occurring in the DNA amplification process in next-generation sequencing, and as a result, have prepared an adaptor having a hairpin structure and capable of self-priming and replicating, that is, a self-priming and replicating hairpin (SelPH) adaptor, and have found that it is possible to prepare libraries by ligation of the SelPH-adaptor of the present invention to an original nucleic acid sample and sequencing after one round of amplification, and at this time, each of the single strands constituting the original nucleic acid sample is made into DNA in duplicate. In addition, the present inventors have found that, when the self-priming and replicating adaptor of the present invention is used, only two rounds of amplification need be performed, and thus it is possible to minimize either jackpot errors caused by several rounds of amplification in the conventional art or errors caused by biased amplification, there is no restriction on the lengths of DNA fragments, paired ends can be made without a self-ligation process of making circular DNA, making the workflow simple and efficient, there is no need to worry about errors and artifacts that may occur due to damage to nucleic acid samples, because there is no use of nicking and USER enzymes, and thus it is possible to reduce the error rate, increase efficiency, and more accurately detect a mutant sequence that is present at a low frequency, compared to a conventional library preparation method, thereby completing the present invention.

Therefore, an object of the present invention is to provide a self-priming and replicating hairpin adaptor for next-generation sequencing (NGS) library preparation.

Another object of the present invention is to provide a method for next-generation sequencing (NGS) library preparation using the self-priming and replicating hairpin adaptor for next-generation sequencing (NGS) library preparation of the present invention.

Still another object of the present invention is to provide a kit for next-generation sequencing (NGS) library preparation comprising the self-priming and replicating hairpin adaptor for next-generation sequencing (NGS) library preparation.

Technical Solution

Therefore, the present invention provides a self-priming and replicating hairpin adaptor for next-generation sequencing (NGS) library preparation comprising: a long single-stranded first oligonucleotide consisting of the nucleotide sequence of SEQ ID NO: 4 and having a hairpin structure; and a short single-stranded second oligonucleotide consisting of the nucleotide sequence of SEQ ID NO: 5.

In one embodiment of the present invention, polymerase may bind to the first oligonucleotide, and the hairpin structure may be maintained even during extension.

In one embodiment of the present invention, the 5' end of the second oligonucleotide consisting of the nucleotide sequence of SEQ ID NO: 5 may not be phosphorylated so that it is not ligated to the 3' end of the first oligonucleotide.

The present invention also provides a method for next-generation sequencing (NGS) preparation comprising steps of: (1) fragmenting genomic DNA to be analyzed; (2) ligating the adaptor of the present invention to an end of the fragmented genomic DNA; (3) adding polymerase to a reaction solution containing the fragmented genomic DNA to which the adaptor of the present invention has been ligated in step (2), followed by an extension reaction to obtain a first reaction product; (4) ligating a universal adaptor for NGS to the first reaction product; (5) adding polymerase to a reaction solution containing the first reaction product to which the universal adaptor for NGS has been ligated in step (4), followed by an extension reaction to obtain a second reaction product; and (6) purifying the second reaction product.

In one embodiment of the present invention, the fragmented genomic DNA and the adaptor of the present invention, which are used in step (2), may be mixed with each other at a molar ratio of 1 (genomic DNA):15 (adaptor) to 1:25.

In one embodiment of the present invention, the method may further comprise, before ligating the adaptor in step (2) and before ligating the universal adaptor for NGS in step (4), a step of adding adenosine to the 3' end of the DNA (A-tailing) after end repair of the DNA.

In one embodiment of the present invention, the first reaction product in step (4) may be an amplification product comprising the nucleotide sequence of the adaptor and having an extended hairpin structure.

In one embodiment of the present invention, the second reaction product in step (5) may be in the form of a linear duplex DNA formed by amplification in the extension reaction.

In an embodiment of the present invention, each of the extension reaction in step (3) and the extension reaction in step (5) may be performed once.

The present invention also provides a kit for DNA library preparation comprising the self-priming and replicating hairpin adaptor for next-generation sequencing (NGS) library preparation according to the present invention.

Advantageous Effects

When the self-priming and replicating hairpin adaptor for NGS library preparation according to the present invention is used, it is possible to minimize the number of amplification reactions, and thus it is possible to minimize either jackpot errors caused by several rounds of amplification in the conventional art or errors caused by biased amplification. In addition, there is no restriction on the lengths of DNA fragments, the workflow is simple and efficient, and there is no need to worry about errors and artifacts that may occur due to damage to a nucleic acid sample because there is no use of separate nicking and USER enzymes. Thus, when the self-priming and replicating adaptor is used for NGS library preparation, it is possible to reduce the error rate, increase efficiency, and more accurately detect a mutant sequence that is present at a low frequency, compared to a conventional library preparation method

DESCRIPTION OF DRAWINGS

FIG. 2 shows the self-priming and replicating hairpin adaptor (a of FIG. 2) according to the present invention, and shows the results of analyzing self-priming and replication (b of FIG. 2) using the self-priming and replicating hairpin adaptor of to the present invention.

Lanes 1, 2 and 3 indicate the products of PCR performed at 54° C., 57° C. and 60° C., respectively.

Figure 5:
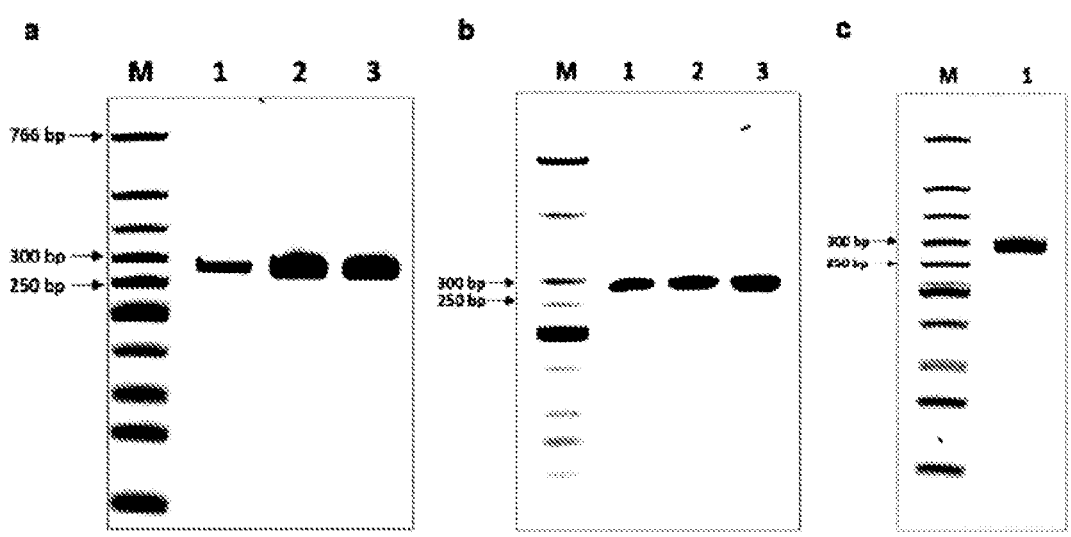

FIG. 5 shows a 285-bp insert DNA construction process and the results of PAGE. a of FIG. 5 shows the results for nested PCR products (PAGE), b of FIG. 5 is a 1.5% agarose gel electrophoresis image for nested PCR products, and c of FIG. 5 shows the results for a gel extraction product.

Figure 6:
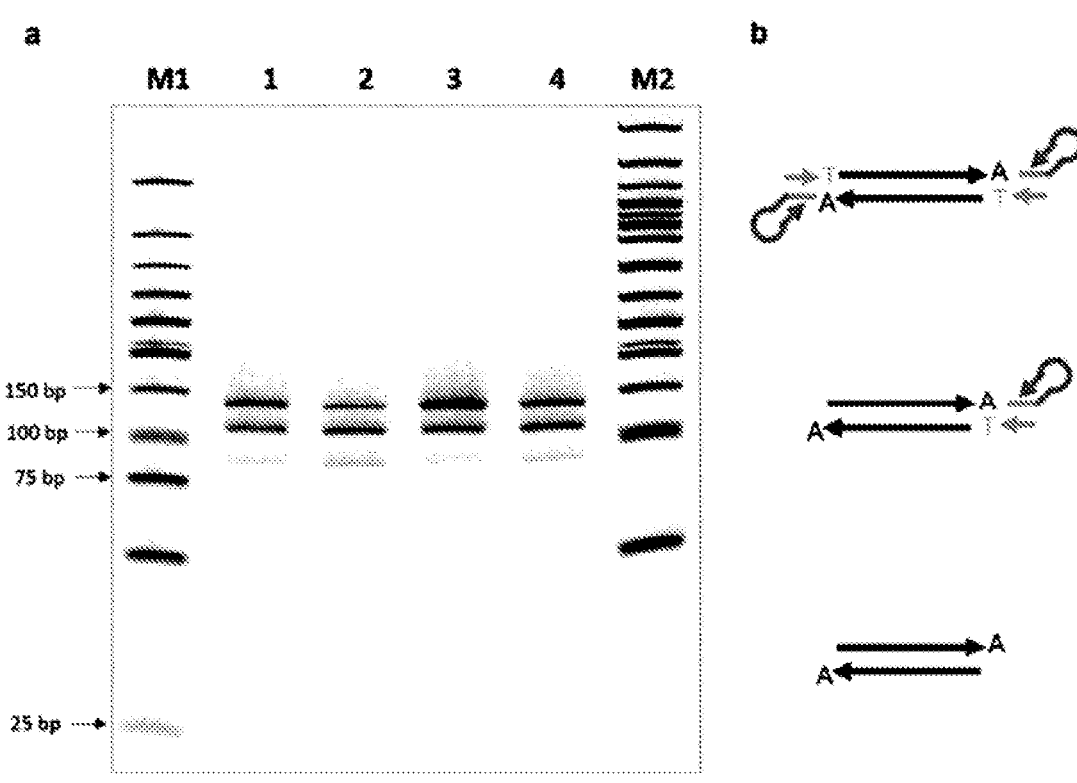

FIG. 6 shows the results of PAGE of ligation products obtained from a 91-bp insert DNA using various ligation regents. In a of FIG. 6, lane 1: NEXTFlex Rapid DNA Sequencing Bundle (Bioo Scientific), lane 2: KAPA Hyper-Plus kit (KAPA Biosystems), lane 3: Illumina's NEBNext Ultra II FS DNA library Prep Kit (NEB), lane 4: blunt/TA Ligase Master Mix (NEB), and M2: 50-bp DNA ladder. b of FIG. 6 schematically shows the production of a SelPH-adaptor ligation product.

Figure 7:
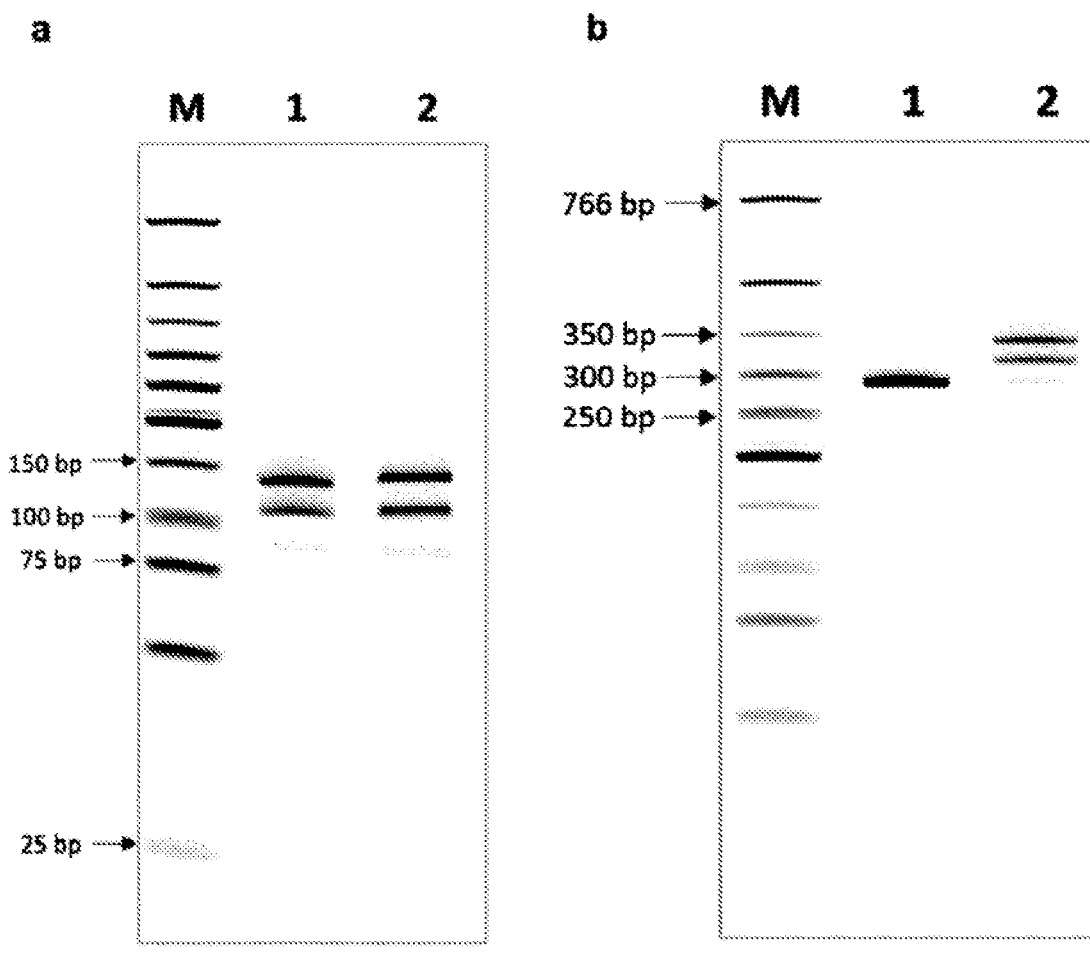

FIG. 7 shows the results of PAGE of ligation products obtained from 91-bp and 285-bp insert DNAs for different ligation times. In a of FIG. 7, lane 1: 91-bp insert DNA ligated for 60 minutes, lane 2: 91-bp insert DNA ligated for 18 hours. In b of FIG. 7, lane 1: 285-bp insert DNA, land 2: 285-bp insert DNA ligated for 1 hour.

Figure 8:
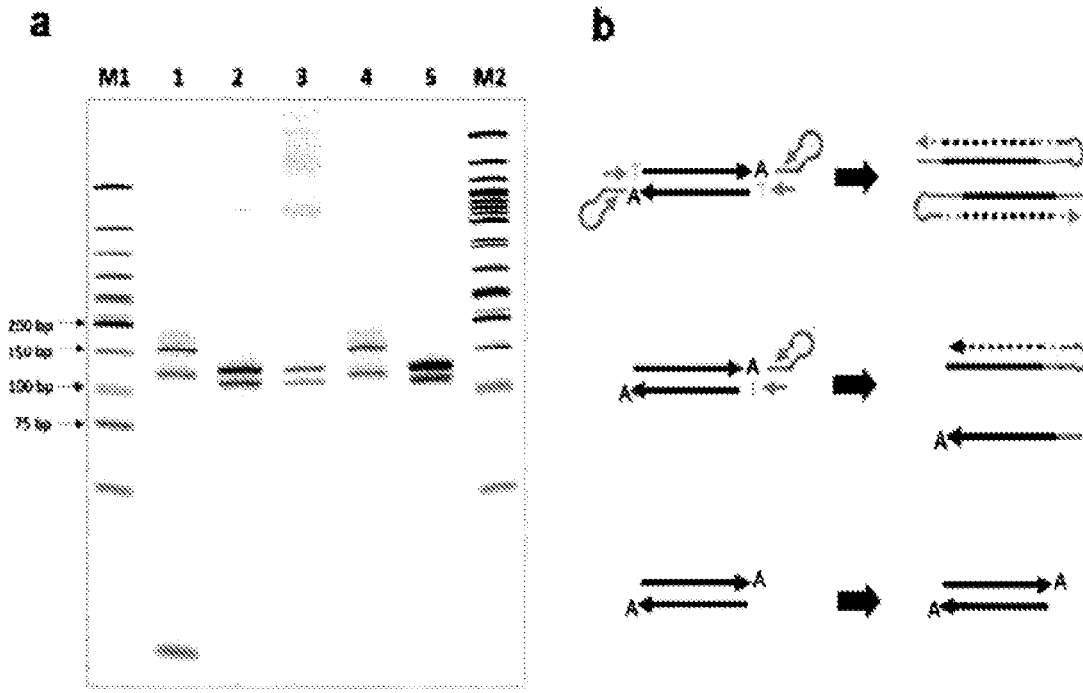

FIG. 8 shows the extension products of 91-bp insert DNA, obtained using different DNA polymerases. In a of FIG. 8, lane1: SelPH-adaptor ligation product, lane 2: a product obtained at a Q5 DNA polymerase annealing temperature of 78° C., lane 3: a product obtained at a Q5 DNA polymerase annealing temperature of 65° C., lane 4: Phi29 DNA polymerase, lane 5: Bst 2.0 DNA polymerase, and M2: 50-bp DNA ladder. b of FIG. 8 schematically shows the results of the first extension reaction.

Figure 9:
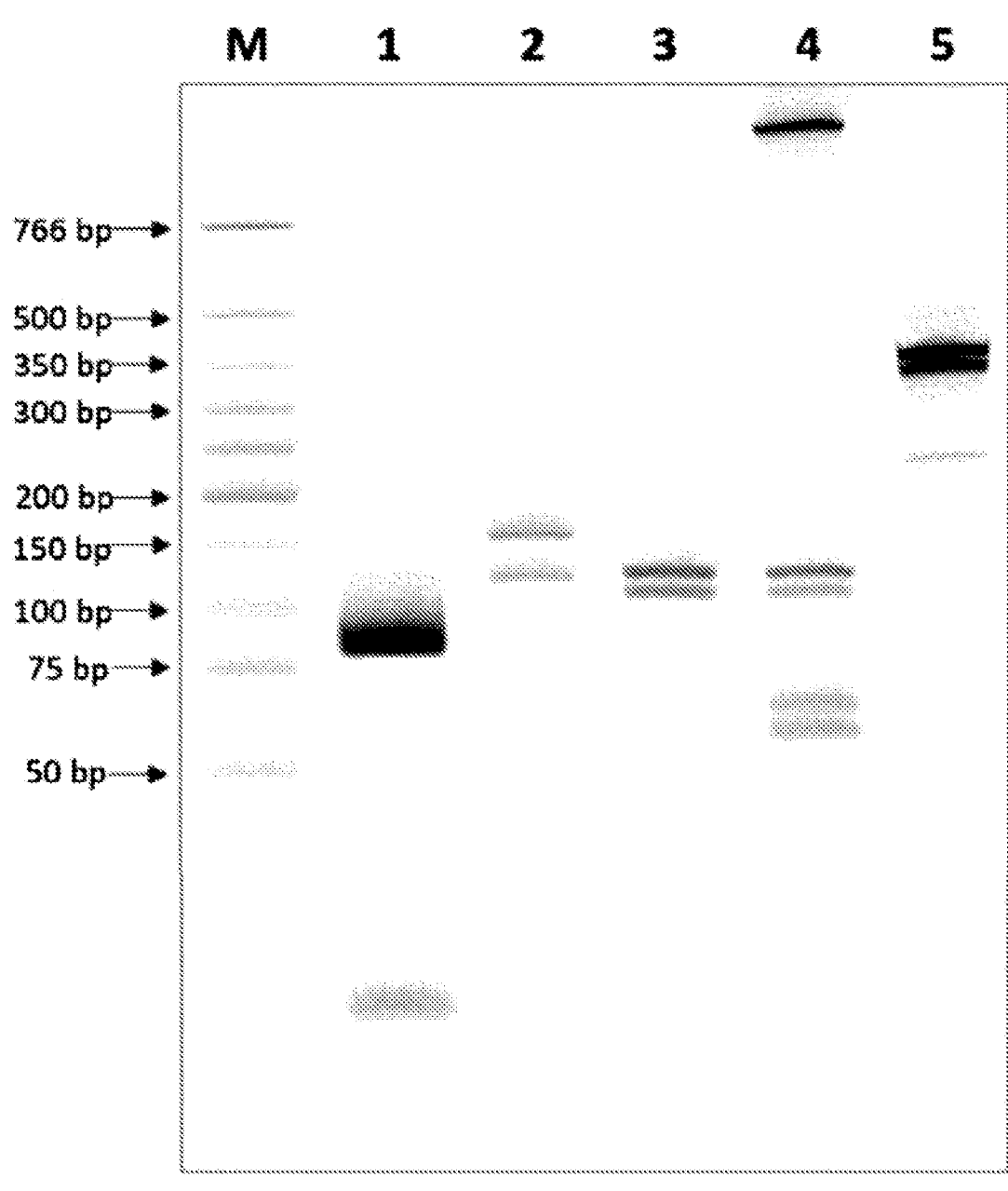

FIG. 9 shows products obtained by performing the entire process of self-priming and replicating hairpin sequencing (SelPH-seq) on 91-bp insert DNA using the SelPH-adaptor of the present invention. Lane 1: SelPH-adaptor and 91-bp insert DNA, lane 2: SelPH-adaptor ligation product, lane 3: first extension reaction product, lane 4: NGS adaptor ligation product, and lane 5: second extension product.

Figure 10:
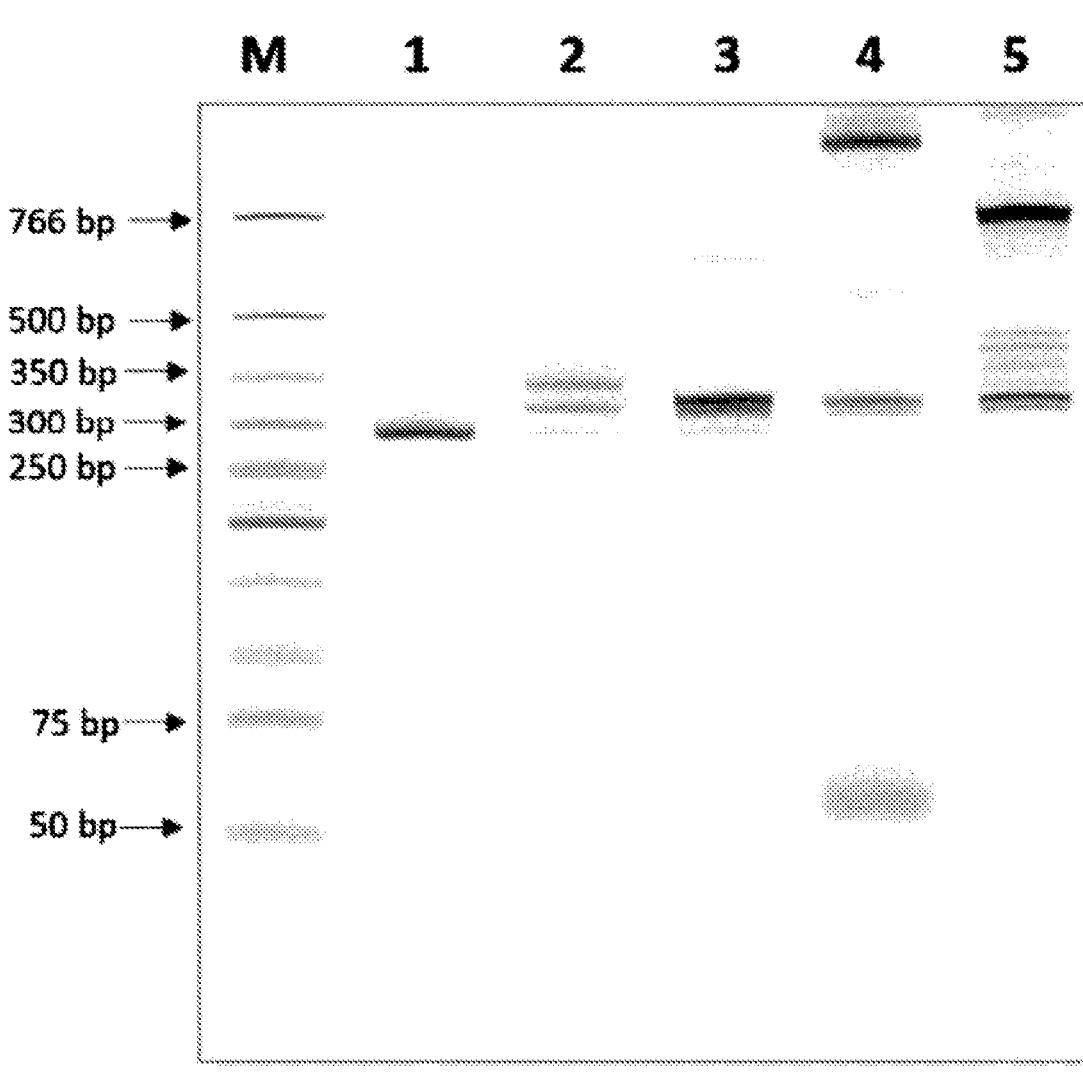

FIG. 10 shows products obtained by performing the entire process of self-priming and replicating hairpin sequencing (SelPH-seq) on 285-bp insert DNA using the SelPH-adaptor of the present invention. Lane 1: 285-bp insert DNA, lane 2: SelPH-adaptor ligation product, lane 3: first extension reaction product, lane 4: NGS adaptor ligation product, and lane 5: second extension reaction product.

Figure 11:
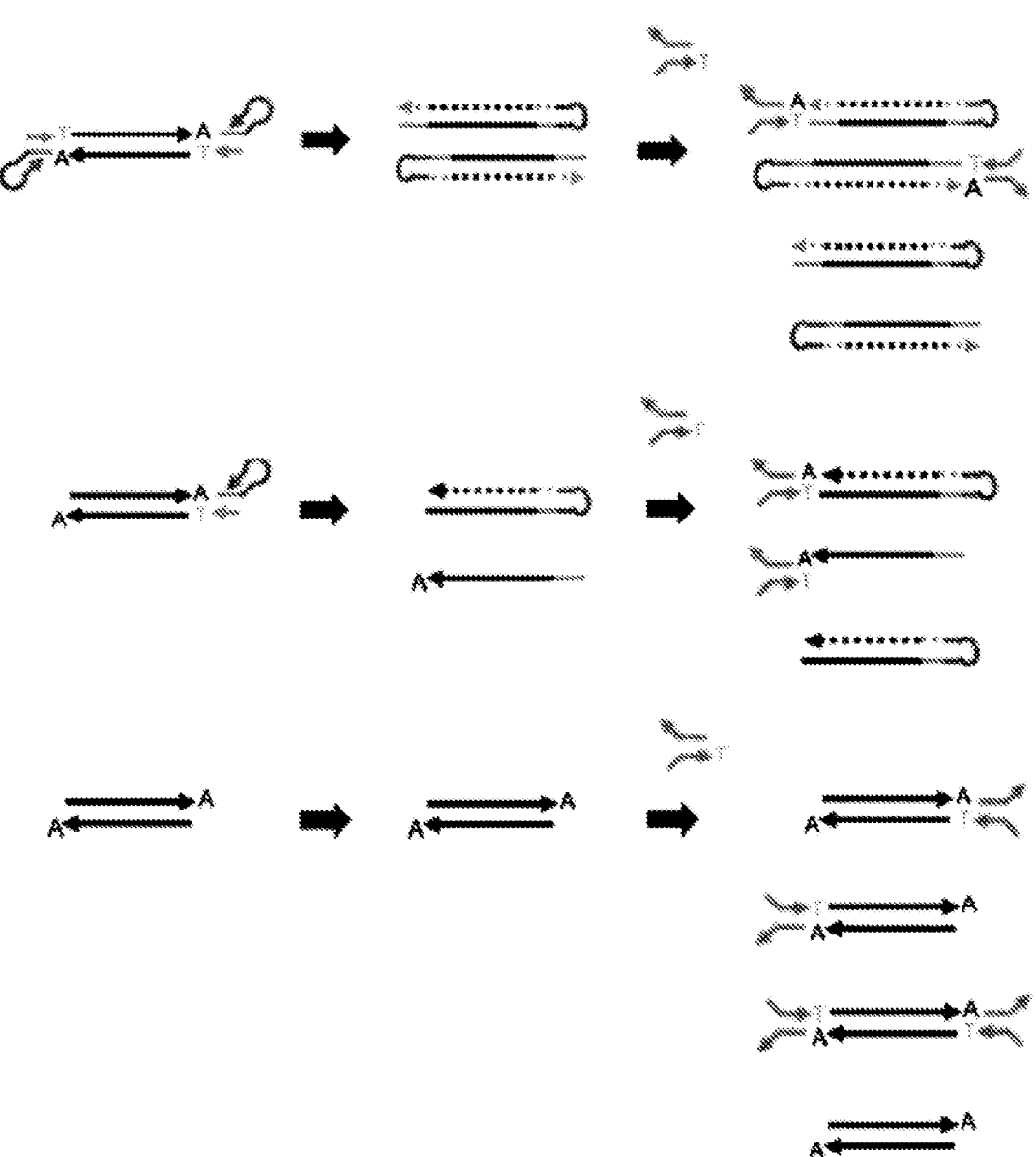

FIG. 11 shows the second ligation reaction process in the self-priming and replicating hairpin sequencing (SelPH-seq) process employing the SelPH-adaptor according to the present invention, and ligation reaction products.

Figure 12:
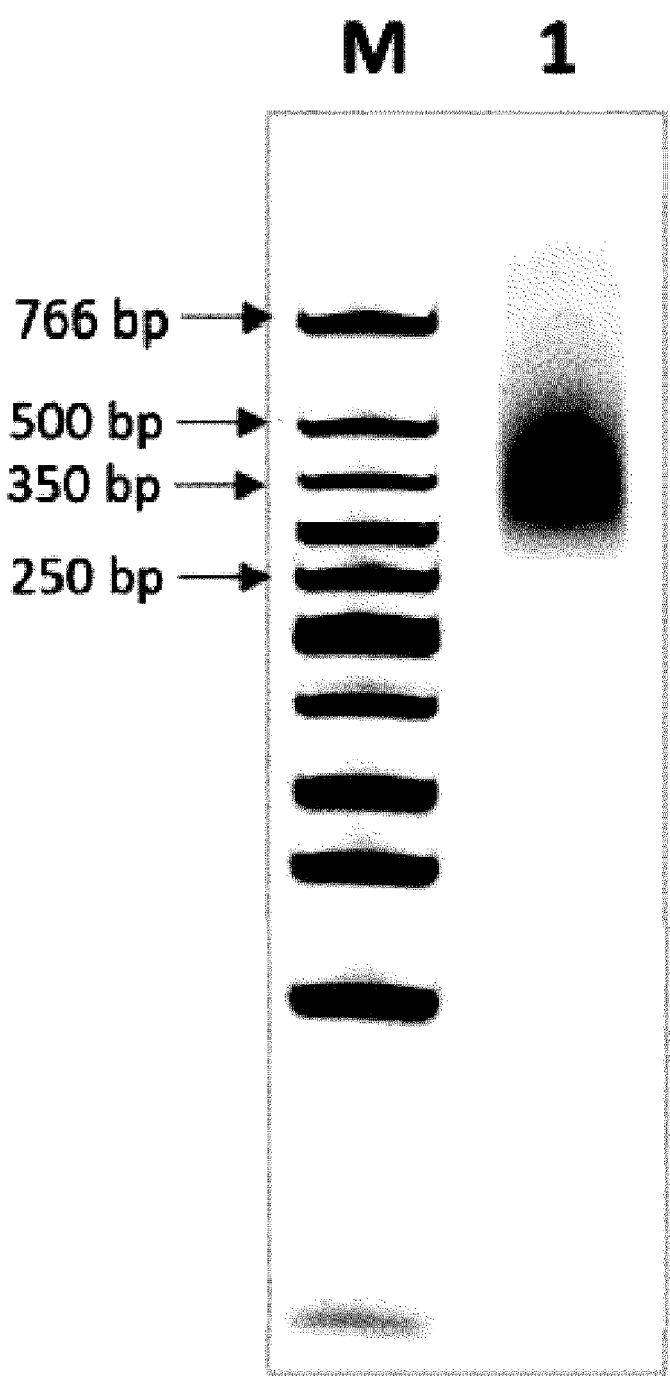

FIG. 12 shows PAGE results for products obtained by performing self-priming and replicating sequencing (SelPH-seq) on the yeast genome using the SelPH-adaptor of the present invention.

BEST MODE

The present invention is characterized by developing a novel adaptor that can minimize errors caused by amplification in the next-generation sequencing (NGS) process and enables the preparation of a next-generation sequencing library even by minimal amplification.

Next-generation sequencing technology is technology that dramatically reduces the time and cost required for genome decoding by producing large amounts of data within a short time, unlike existing methods. Sequencing platforms for next-generation sequencing technology have been developed, analysis costs for the next-generation sequencing technology have gradually become cheaper over time, and next-generation sequencing technology has succeeded in finding genes responsible for diseases such as genetic disorders, rare diseases, cancer, etc. According to Illumina's next-generation sequencing technology which is currently most frequently used, DNA is extracted from a sample, subjected to mechanical fragmentation, and then prepared into a library having a specific size, and the library is used for sequencing. Next, initial sequencing data are produced. by repeating four kinds of complementary nucleotide binding and isolation reactions with one base unit by using a high-throughput sequencing system, followed by analysis steps using bioinformatics such as trimming of initial data, mapping, identification of genome mutation, and analysis of mutation information.

This next-generation sequencing method is also contributing to the creation of new added values through the development of new disease treatments by discovering genomic mutations that have an effect on or may have a high possibility of affecting diseases and various biological forms.

Meanwhile, as mentioned in the "Background Art" section, a process of preparing a library sample through polymerase chain reaction (PCR) is very important for library preparation in the next-generation sequencing method, and currently developed technologies have a problem in that they show a high error rate in this process.

In addition, in conventional library preparation, a library required for sequencing is prepared by ligating an adaptor to random DNA or cDNA fragments of a sample in the 5' to 3' direction, and in this process, there is a problem of biased amplification or noise generation. In addition, there is a problem in that this process is expensive, and when barcodes are used, a problem arises in that PCR amplification bias and the complexity of the workflow increase due to the presence of the barcodes. In addition, a problem arises in that it is difficult to detect rare mutations.

Therefore, the present inventors have developed an adaptor for NGS library preparation which can minimize errors caused by an amplification reaction, exhibits high accuracy even given minimal amplification, has no limitation in terms of the lengths of DNA fragments, has no worry about DNA damage, and can accurately detect mutant sequences present at low frequencies.

Therefore, the present invention is characterized by providing a self-priming and replicating hairpin adaptor for next-generation sequencing (NGS) library preparation comprising: a long single-stranded first oligonucleotide consisting of the nucleotide sequence of SEQ ID NO: 4 and having a hairpin structure; and a short single-stranded second oligonucleotide consisting of the nucleotide sequence of SEQ ID NO: 5.

The adaptor of the present invention comprises the long single-stranded first oligonucleotide and the short single-stranded second oligonucleotide. Here, polymerase may bind to the first oligonucleotide, and the hairpin structure may be maintained even during an extension reaction because the first oligonucleotide contains a self-priming and replicating hairpin-domain (SelPH-domain), that is, a self-priming and replicating nucleotide sequence. The nucleotide sequence corresponding to the SelPH-domain according to the present invention corresponds to a sequence of the nucleotides at positions 17 to 28 (GCGA CGAC ATCT) and a sequence of the nucleotides at positions 33 to 44 (AGAT GTCG TCGC) in the nucleotide sequence of SEQ ID NO: 4. The nucleotide sequence of the SelPH-domain consists of a nucleotide sequence in which the sequence of nucleotides at positions 17 to 28 and the sequence of nucleotides at positions 33 to 44 are complementary to each other.

In addition, the 5' end of the first oligonucleotide is phosphorylated.

The second oligonucleotide is not phosphorylated at the 5' end so as not to be ligated to the 3' end of the first oligonucleotide, and specifically, it consists of the nucleotide sequence of SEQ ID NO: 5.

The adaptor for NGS library preparation according to the present invention is characterized by being capable of self-priming and replicating, and having a hairpin structure. Here, "self-priming and replicating" means that, when polymerase binds to the nucleotide sequence of the adaptor of the present invention, the nucleotide sequence of the adaptor is amplified by the polymerase. That is, the adaptor for NGS library preparation according to the present invention has a hairpin structure having a complementary nucleotide sequence, and after polymerase binds to the adaptor, amplification starts from the site corresponding to the complementary nucleotide sequence and occurs up to the DNA to which the adaptor is ligated. In the annealing step of the polymerase chain reaction (PCR) in a conventional method, the polymerase extension reaction may occur only after primers bind to the template strand DNA under a condition where the primers have specific nucleotide sequences. However, the self-priming and replicating by the adaptor of the present invention is characterized by enabling the polymerase chain reaction due to the hairpin structure having a complementary nucleotide sequence without a separate process of binding between the primers and the template strand DNA. That is, the hairpin structure itself of the adaptor of the present invention may serve as a primer.

In one example of the present invention, in order to confirm the self-priming ability of the adaptor of the present invention, analysis was performed using Q5 DNA polymerase to determine whether the adaptor has self-priming ability and to determine optimal conditions. To this end, among the two oligonucleotides constituting the adaptor, long single-stranded oligonucleotides with different lengths were prepared (see Table 6), and then the degree of self-priming by an extension reaction (amplification reaction) was analyzed.

As a result, it could be confirmed that the adaptor having the self-priming hairpin (SelPH) domain in which the hairpin stem in the long single-stranded oligonucleotide consists of 12-bp nucleotides, that is, the adaptor having the self-priming nucleotide sequence, had higher stability and better self-priming ability than adaptors having hairpin stem lengths of 8 bp and 10 bp. Thereby, it was confirmed that the adaptor of the present invention is self-primed from a single-stranded oligonucleotide.

Therefore, the long single-stranded first oligonucleotide consisting of the nucleotide sequence of SEQ ID NO: 4 including the SelPH-domain is characterized in that polymerase can well bind thereto and the hairpin structure can be well formed and maintained even during an extension reaction.

In addition, the long single-stranded first oligonucleotide of the present invention contained 4 adenines between the end of the hybridization stem and the beginning of the SelPH-domain so that the 3' end of the SelPH-domain and the 5' end of the short single-stranded second oligonucleotide would not be ligated to each other during the adaptor ligation process (see FIG. 2).

Furthermore, the present invention may provide a method for NGS library preparation using the self-priming and replicating hairpin adaptor for NGS (next-generation sequencing) library preparation.

The method for NGS library preparation according to the present invention largely comprises: phase I of ligating the adaptor for NGS library preparation according to the present invention to genomic DNA to be analyzed, followed by an extension reaction; and phase II of ligating an universal adaptor for NGS to the product of the first extension reaction, followed by an extension reaction.

Preferably, the method for next-generation sequencing (NGS) preparation according to the present invention comprises steps of: (1) fragmenting genomic DNA to be analyzed; (2) ligating the adaptor of the present invention to an end of the fragmented genomic DNA; (3) adding polymerase to a reaction solution containing the fragmented genomic DNA to which the adaptor of the present invention has been ligated in step (2), followed by an extension reaction to obtain a first reaction product; (4) ligating a universal adaptor for NGS to the first reaction product; (5) adding polymerase to a reaction solution containing the first reaction product to which the universal adaptor for NGS has been ligated in step (4), followed by an extension reaction to obtain a second reaction product; and (6) purifying the second reaction product.

Here, phase I refers to steps (1) to (3), and phase II refers to steps (4) to (6).

Hereinafter, each step will be described in detail.

First, in step (1), the genomic DNA to be analyzed is fragmented.

Here, the DNA to be analyzed may include genomic DNA derived from any organisms to be analyzed, such as all mammals including humans, plants, microorganisms, and fungi, and the DNA may be obtained and fragmented by a conventional method known in the art.

Then, in step (2), the adaptor of the present invention is ligated to an end of the fragmented genomic DNA to be analyzed.

Here, the fragmented genomic DNA to be analyzed and the adaptor of the present invention may be mixed with each other at a mixing ratio of 1:15 to 1:25 and ligated to each other.

In the process of preparing a library for next-generation sequencing, ligation of the adaptor to a target DNA and extension reactions are very important. In the present invention, an experiment was conducted to determine the amounts of DNA and the adaptor of the present invention for optimization of ligation and extension reactions, and as a result, it was confirmed that the mixing ratio between the genomic DNA to be analyzed to the adaptor of the present invention was preferably 1:15 to 1:25, most preferably 1:20.

If the mixing ratio is out of the above-described ratio, the efficiency of ligation and extension reactions may be insufficient, and thus the desired effect cannot be obtained.

In addition, an experiment was conducted to determine the optimal ligation reaction time. As a result of conducting experiments with ligation times of 15 minutes, 60 minutes, and 18 hours, respectively, it was confirmed that the most suitable ligation time was 15 minutes.

In addition, before ligating the adaptor of the present invention to the end of the fragmented genomic DNA to be analyzed, a step of adding adenosine to the 3' end of the DNA (A-tailing) after end repair of the DNA may be performed.

After completion of ligation of the adaptor of the present invention, step (3) is performed. In step (3), polymerase is added to a reaction solution containing the fragmented genomic DNA to which the adaptor of the present invention has been ligated in step (2), and an extension reaction is performed to obtain a first reaction product.

The polymerase may be any polymerase that is used for amplification of nucleic acids in the art. Specifically, the polymerase may be Q5 DNA polymerase, Phi29 DNA polymerase, or Bst 2.0 DNA polymerase, without being limited thereto.

In the present invention, the extension reaction in step (3) is performed for only one cycle, and the first reaction product obtained through the extension reaction has an amplification product including the adaptor nucleotide sequence of the present invention and having a hairpin structure.

That is, when the adaptor of the present invention is ligated by ligase to the fragmented nucleic acid sample to be analyzed and polymerase is added to the sample, replication occurs by an extension reaction from the 3' end through the stem portion of the hybridized adaptor to the 5' end, due to the self-priming and replicating nucleotide sequence (SelPH-domain) contained in the adaptor of the present invention. As a result, single strands of the nucleic acid sample to be analyzed are separated from each other to produce a long hairpin-shaped first reaction product (see phase I in FIG. 1).

After completion of phase I, phase II is performed. Specifically, step (4) of ligating the universal adaptor for NGS to the first reaction product is performed.

Here, before ligation of the universal adaptor for NGS, an end repair and A-tailing step of adding adenosine to the 3' end of DNA of the first reaction product for ligation of the universal adaptor for NGS may be performed.

As the universal adaptor for NGS, any adaptor for NGS known in the art may be used, and in one example, Bioo Scientific's NEXTFlex DNA barcode adaptor was used.

The ligation may be performed using any ligase known in the art.

After completion of ligation of the universal adaptor for NGS to the first reaction product, step (5) is performed, in which polymerase is added to the reaction solution containing the first reaction product to which the universal adaptor for NGS has been ligated, followed by an extension reaction to obtain a second reaction product.

The polymerase used in this step may be any polymerase that is used for amplification of nucleic acids in the art. Specifically, the polymerase may be Q5 DNA polymerase, Phi29 DNA polymerase, or Bst 2.0 DNA polymerase, without being limited thereto. The extension reaction to obtain the second reaction product is performed for only one cycle.

In addition, in the extension reaction to obtain the second reaction product, a primer (e.g., P7 primer) for attachment to a flow cell may be used together with the polymerase, and as the first reaction product having a long hairpin structure is replicated, linear duplex DNA is obtained as the second reaction product.

In one example of the present invention, the first reaction product was replicated and amplified into a duplex DNA having P5 and P7 at both ends of the second reaction product.

The second reaction product amplified by the above method may be subjected to a purification step, and any general method known in the art may be used for purification of the amplified product. For example, gel filtration, a method using a column, or a method using an electromagnetic field may be used, without being limited thereto.

In the present invention, the "extension reaction" refers to a reaction for amplifying the nucleic acid sample to be analyzed. Various amplification reactions for amplification of nucleic acid samples have been reported in the art, and examples thereof include, but are not limited to, polymerase chain reaction (PCR), reverse transcription-polymerase chain reaction (RT-PCR), ligase chain reaction, repair chain reaction, transcription-mediated amplification (TMA), self-sustained sequence replication, random priming and replicating polymerase chain reaction, nucleic acid sequence-based amplification, strand displacement amplification, and loop-mediated isothermal amplification.

Furthermore, the present invention may provide a kit for DNA library preparation comprising the self-priming and replicating hairpin adaptor for next-generation sequencing (NGS) library preparation according to the present invention.

The kit according to the present invention may optionally comprise a buffer, a DNA polymerase, and reagents necessary for performing a PCR reaction for target amplification, and may comprise various polynucleotide molecules, reverse transcriptase, various buffers and reagents, etc.

As described above, the adaptor for next generation sequencing (NGS) library preparation provided by the present invention is an adaptor having a hairpin structure and capable of self-priming and replicating. A library can be prepared very quickly and accurately by ligating the SelPH-adaptor of the present invention to a nucleic acid sample to be analyzed, performing one round of amplification, and then performing a known sequencing method.

In addition, when the self-priming and replicating adaptor of the present invention is used, only two rounds of amplification (amplification in phase I by an extension reaction after ligation of the adaptor of the present invention, and amplification in phase II by an extension reaction after ligation of the universal adaptor for NGS) may be performed, and thus it is possible to minimize either jackpot errors caused by several rounds of amplification or errors caused by biased amplification.

In addition, when the self-priming and replicating adaptor of the present invention is used, there is no restriction on the lengths of DNA fragments, a product in the form of paired ends can be made without a self-ligation process of making circular DNA, making the workflow simple and efficient, and there is no need to worry about errors and artifacts that may occur due to damage to nucleic acid samples, because there is no use of nicking and USER enzymes.

Therefore, when a library for NGS is prepared using the self-priming and replicating adaptor of the present invention, it is possible to increase the efficiency while reducing the error rate, and more accurately detect a mutant sequence present at a low frequency, compared to a conventional library preparation method.

MODE FOR INVENTION

Hereinafter, the present invention will be described in more detail with reference to examples. These examples are for explaining the present invention in more detail, and the scope of the present invention is not limited to these examples.

Preparation Example

Reagents

All oligonucleotides were purchased from IDT (Integrated DNA Technology), and lyophilized oligonucleotides were diluted with 0.1M TE buffer, and then allowed to react in mixing blocks (MB102: Bioer) at a temperature of 50° C. for 1 hour. For post-ligation cleanup and post-amplification cleanup, Promega's ProNex size-selective purification system was used. 5×Q5 reaction buffer, 5× high-fidelity DNA polymerase, Bst 2.0 DNA polymerase, 10× isothermal amplification buffer, each 10 mM dNTPs, and Illumina's NEBNext Ultra II FS DNA library Prep kit used for yeast genome library preparation were purchased from NEB (New England Biolabs). In experiments on 91-bp and 285-bp insert DNAs, Bio Scientific's NEXTflex Rapid DNA sequencing bundle was used.

Experimental Methods

① Confirmation of Self-Priming and Replication

After the sequence of exon 21 of the EGFR gene was searched in NCBI, each of three hairpin-shaped adaptor sequences for self-priming and replicating were ligated to the 3' end of an oligonucleotide having 40 nucleotides (nucleotide positions 6 to 46) as shown in Table 1 below. Oligonucleotides were diluted to a concentration of 100 μM using 1M TE buffer and incubated. 5 μl of 5×Q5 reaction buffer, 0.5 μl of each of 10 mM dNTPs, 0.25 μl of Q5 DNA polymerase, and 1 μl of each oligonucleotide diluted to 20 μM in distilled water were added to reach a total volume of 25 μl. The reaction mixture was allowed to react at 98° C. for 10 seconds, 65° C. for 30 seconds, and then 72° C. for 10 minutes.

TABLE 1

| Name | Oligonucleotide sequence (5' to 3') | |
|---|---|---|
| 8-bp adaptor | GAACT ACTTG GAGGA CCGTC GCTTG GTGCA CCGCG ACCTG CGAC ATCT AAAA AGAT GTCG | SEQ ID NO: 1 |
| 10-bp adaptor | GAACT ACTTG GAGGA CCGTC GCTTG GTGCA CCGCG ACCTG GC ACAC ATCT AAAA AGAT GTGT GC | SEQ ID NO: 2 |
| 12-bp adaptor | GAACT ACTTG GAGGA CCGTC GCTTG GTGCA CCGCG ACCTG GCGA CGAC ATCT AAAA AGAT GTCG TCGC | SEQ ID NO: 3 |

② Preparation of SelPH-Adaptor

For a long single strand and short single strand constituting a SelPH-adaptor, each of oligonucleotides shown in Table 2 below was reacted with 0.1M TE buffer at a concentration of 100 μM, and then adjusted to a final concentration of 30 μM and a total volume of 100 μl using 2×PBS. Then, annealing was performed by lowering the temperature slowly from 95° C. to 20° C. using a thermocycler.

TABLE 2

| | SelPH-adaptor sequence | |
|---|---|---|
| Name | Oligonucleotide sequence (5' to 3') | |
| SelPH- adaptor long strand | /5Phos/GGAT AAGG GAGC AAAA GCGA CGAC ATCT AAAA AGAT GTCG TCGC | SEQ ID NO: 4 |

TABLE 2-continued

| | SelPH-adaptor sequence | |
|---|---|---|
| Name | Oligonucleotide sequence (5' to 3') | |
| SelPH- adaptor short strand | GCTC CCTT ATCC T | SEQ ID NO: 5 |

③ SelPH-Sequencing

SelPH-sequencing was performed using insert DNAs constructed to have sizes of 91 bp and 285 bp, respectively.

(i) Experiment on 91-Bp Insert DNA

Construction of 91-Bp Insert DNA

Each of single-stranded oligonucleotides constituting the 91-bp insert DNA shown in Table 3 below was diluted to 20 μM using 1M TE buffer, and adjusted to a final concentration of 1 μM and a total volume of 100 μl using 1×PBS buffer, and then annealed by lowering the temperature slowly from 95° C. and 20° C. using a SimpliAmp Thermal Cycler (Thermo Fisher Scientific).

TABLE 3

| Name | Oligonucleotide sequence (5' to 3') | |
|---|---|---|
| 91-bp single strand 1 | /5Phos/GGCAT GAACT ACTTG GAGGA CCGTC GCTTG GTGCA CCGCG ACCTG GCAGC CAGGA ACGTA CTGGT GAAAA CACCG CAGCA TGTCA AGATC A | SEQ ID NO: 6 |
| 91-bp single strand 2 | /5Phos/GATCT TGACA TGCTG CGGTG TTTTC ACCAG TACGT TCCTG GCTGC CAGGT CGCGG TGCAC CAAGC GACGG TCCTC CAAGT AGTTC ATGCC A | SEQ ID NO: 7 |

First Ligation (SelPH-Adaptor)

Ligation of the SelPH-adaptor was performed using 18 μl of 1 μM 91-bp insert DNA 18 μl, 15 μl of NEXTFlex End-Repair & Adenylation buffer mix, and 0.5 μl of 25 μM SelPH-adaptor according to the manufacturer's protocol.

Post-Ligation Cleanup

A 3× volume of ProNex Chemistry reagent was added to the SelPH-adaptor ligation sample, and the experiment was conducted according to the manufacturer's protocol, and 40 μl of elution buffer was added to the mixture, followed by 10 minutes of elution.

First Extension Reaction

2 μl of 10× isothermal amplification buffer, each 0.5 μl of 10 mM dNTPs, 0.5 μl of Bst 2.0 DNA polymerase, and 10 μl of the eluted sample were mixed together and adjusted to a total volume of 20 μl using distilled water. The mixture was allowed to react at 65° C. for 10 minutes, and Bst DNA polymerase was added thereto, followed by reaction at 65° C. for 5 minutes.

Post-Amplification Cleanup

A 3× volume of ProNex Chemistry reagent was added to the SelPH-adaptor ligation sample, and the experiment was conducted according to the manufacturer's protocol, and 20 μl of elution buffer was added to the mixture, followed by 10 minutes of elution.

End Repair and A-Tailing

15 μl of NEXTFlex end-repair and adenylation buffer mix and 3 μl of NEXTFlex end-repair and adenylation enzyme mix were added to the eluted sample, and the experiment was conducted according to the manufacturer's instructions.

Second Ligation (NGS-Adaptor)

The NGS-adaptor contained in Bioo Scientific's NEXT-Flex Rapid DNA Sequencing Bundle was used. 2.5 µl of 25 µM NGS-adaptor was added to the sample subjected to A-tailing, and the experiment was conducted according to the manufacturer's instructions.

Post-Ligation Cleanup

A 2× volume of ProNex Chemistry reagent was added to the sample subjected to NGS-adaptor ligation, and the experiment was conducted according to the manufacturer's instructions, and 40 µl of elution buffer was added to the mixture, followed by 10 minutes of elution.

Second Extension Reaction

4 µl of 10× isothermal amplification buffer, each 0.5 µl of 10 mM dNTPs, 0.5 µl of Bst 2.0 DNA polymerase, and 30 µl of the eluted sample were mixed together and adjusted to a total volume of 40 µl using distilled water. 2.5 µl of the PCR primer shown in Table 4 according to the oligonucleotide sequence provided by Bioo Scientific was added to the mixture. The mixture was allowed to react at 65° C. for 10 minutes, and then Bst DNA polymerase was added thereto, followed by reaction at 65° C. for 5 minutes.

TABLE 4

| Illumina's P7 primer | |
| --- | --- |
| Name | Oligonucleotide sequence (5' to 3') |
| NEXTflex PCR primer | CAAGC AGAAG ACGGC ATACG AGAT (SEQ ID NO: 9) |

Post-Amplification Cleanup

A 1.3× volume of ProNex Chemistry reagent was added to the sample subjected to the second extension reaction, and the experiment was conducted according to the manufacturer's instructions. 30 µl of elution buffer was added to the mixture, followed by 10 minutes of elution.

(ii) Experiment on 285-Bp Insert DNA

Preparation of 285-Bp Insert

To obtain a 285-bp DNA fragment that targets position 1041 of the BRCA1 gene, the primers shown in Table 5 were prepared.

TABLE 5

| BRCA1 gene position 1041 primer (285 bp) | |
| --- | --- |
| Name | Oligonucleotide sequence (5' to 3') |
| Forward primer | /5Phos/CTGAA TTCTG TAATA AAAGC (SEQ ID NO: 10) |
| Reverse primer | /5Phos/CATCA GAACC TAACA GTTCA (SEQ ID NO: 11) |

20 ng of human genomic DNA, 5 µl of 5×Q5 reaction buffer, 0.5 µl of each of 10 mM dNTPs, each of 10 µM forward primer and reverse primer (final concentration: 0.5 µM), and 0.25 µl of Q5 High-fidelity DNA polymerase were mixed together, and the mixture was subjected to PCR under the following conditions: initial denaturation at 98° C. for 30 sec, and then 35 cycles, each consisting of denaturation at 54° C. for 10 sec, annealing at 57° C. for 30 sec, and extension at 60° C. for 30 sec, followed by final extension at 72° C. for 2 min. Several faint bands were identified on the PAGE image, and thus nested PCR was performed on the same sample under the same conditions, followed by electrophoresis. As a result, a single band was identified. After electrophoresis of the sample on 1.5% agarose gel, a 285-bp insert DNA was prepared using the Monarch Gel Extraction kit (NEB). Thereafter, the sample was subjected to PAGE again and a single band was identified on the gel, and then the concentration was measured using NanoDrop (DeNO-VIX).

End Repair and A-Tailing

The reaction was performed using 400 ng of the 285-bp insert DNA according to the manufacturer. Subsequent experiments were conducted in the same manner as the experiments conducted using the 91-bp insert DNA.

(iii) Optimization of Ligation Conditions

Both 91-bp and 285-bp insert DNAs were used, which were each annealed at a concentration of 1 µM in 1×PBS buffer and used without further dilution. After ligation, purification was performed using the ProNex size-selective purification system, followed by PAGE analysis.

Comparison of Four Reagents for NGS Library Preparation

Experiments were conducted using four commercially available reagents for NGS library preparation, and since the experimental methods were different between the reagents, the experiments were performed according to the instructions of each manufacturer, but the mixing ratio between 91-bp insert DNA and SelPH-adaptor used was set to a ratio of 1:20. During purification using the ProNex Size-selective purification system, the volume ratio between ProNex Chemistry reagent and the sample was 3×, and the elution time was 10 minutes.

(a) NEXTFlex Rapid DNA Sequencing Bundle (Bioo Scientific)

3 µl of 91-bp insert DNA, 2.5 µl of 25 µM SelPH-adaptor, 15 µl of EXTFlex end-repair and adenylation buffer mix, and 47.5 µl of NEXTFlex ligase enzyme mix were mixed together, and distilled water was added thereto to reach a total volume of 100 µl. Experimental conditions such as reaction time followed the manufacturer's instructions, and the elution volume during purification was set to 40 µl.

(b) KAPA HyperPlus Kit (KAPA Biosystems)

3.5 µl of 91-bp insert DNA, 5 µl of 15 µM SelPH-adaptor, 5 µl of 10×KAPA Frag buffer, 7 µl of end-repair and A-tailing buffer, 30 µl of ligation buffer, and 10 µl of DNA ligase were mixed together and distilled water was added thereto to reach a total volume of 110 µl. Experimental conditions such as reaction time followed the manufacturer's instructions, and the elution volume during purification was set to 40 µl.

© Illumina's NEBNext Ultra II FS DNA Library Prep Kit (NEB)

5 µl of 91 bp insert DNA, 2.5 µl of 15 µM SelPH-adaptor, 7 µl of NEBNext Ultra II FS reaction buffer, 30 µl of NEBNext Ultra II ligation master mix, and 1 µl of NEBNext ligation enhancer were mixed together and distilled water was added thereto to reach a total volume of 68.5 µl. Experimental conditions such as reaction time followed the manufacturer's instructions, and the elution volume during purification was set to 30 µl.

(d) Blunt/TA Ligase Master Mix (NEB)

1 µl of 91 bp insert DNA, 3 µl of 30 µM SelPH-adaptor, and 10 µl of Blunt/TA Ligase Master Mix were mixed together and distilled water was added thereto to reach a total volume of 20 µl with distilled water. Experimental conditions such as reaction time followed the manufacturer's instructions, and the elution volume during purification was set to 15 µl.

Ligation Time 91-bp and 285-bp insert DNAs and the ligation reagent of NEXTFlex Rapid DNA Sequencing Bundle (Bioo Scientific) were used, and experiments were performed according to the manufacturer's instructions for different reaction times. In the case of 91-bp insert DNA, the ligation time was increased from 15 minutes to 60 minutes and 18 hours, and in the case of 285-bp insert DNA, the ligation time was increased to 60 minutes. Purification was performed using the ProNex Size-selective purification system, and during purification, the volume ratio between ProNex Chemistry reagent and the sample was 3×, the elution time was 10 minutes, and the elution volume was 40 µl.

(iv) Optimization of Extension Conditions

The sample subjected to purification after ligation with 1 µg of 91-bp insert DNA with 2.5 µl of 25 µM SelPH-adaptor was used.

Q5 DNA Polymerase

8 µl of SelPH-adaptor ligation sample, 5 µl of 5×Q5 reaction buffer, each 0.5 µl of 10 mM dNTPs, and 0.25 µl of Q5 DNA polymerase were mixed together, and distilled water was added thereto to reach a total volume of 25 µl, thereby preparing two samples. Each sample was subjected to PCR under the following conditions: initial denaturation at 98° C. for 30 sec, and then one cycle consisting of denaturation at 78° C. for 10 sec, annealing at 65° C. for 15 sec, and extension at 72° C. for 30 sec, followed by final extension at 72° C. for 5 minutes.

Phi29 DNA Polymerase

8 µl of SelPH-adaptor ligation sample, 2 µl of 10× Phi29 DNA polymerase reaction buffer, each 0.5 µl of 10 mM dNTPs, 0.2 µl of 100×BSA, and 0.2 µl of Phi29 DNA polymerase were mixed together, and distilled water was added thereto to reach a total volume of 20 µl. Next, the mixture was allowed to react at 30° C. for 5 minutes, and then Phi29 DNA polymerase was added thereto, followed by reaction at 30° C. for 10 minutes and inactivation at 65° C. for 10 minutes, and then the temperature was lowered slowly to 20° C.

Bst 2.0 DNA Polymerase

8 µl of SelPH-adaptor ligation sample, 2 µl of 10× isothermal amplification buffer, 0.5 µl of each of 10 mM dNTPs, and 0.5 µl of Bst 2.0 DNA polymerase were mixed together, and distilled water was added thereto to reach a total volume of 20 µl. Next, the mixture was allowed to react at 65° C. for 10 minutes, and then Bst 2.0 DNA polymerase was added thereto, followed by reaction at 65° C. for 10 minutes and inactivation at 80° C. for 20 minutes, and then the temperature was lowered slowly to 20° C.

④ Preparation of Yeast Genomic Library Using SelPH-Seq

The genomic DNA of *Saccharomyces cerevisiae* (By4741), a yeast strain of about 12 Mb, was used at a concentration of 446.745 ng/µl. An experiment was conducted Illumina's NEBNext Ultra II FS DNA library prep kit (NEB) according to the manufacturer's instructions.

DNA Fragmentation, End Repair and A-Tailing 0.5 µl of yeast genomic DNA, 7 µl of NEBNext Ultra II FS reaction buffer, and 2 µl of NEBNext Ultra II FS enzyme mix were mixed together, and distilled water was added thereto to reach a total volume of 35 µl. Next, the mixture was allowed to react at 37° C. for 40 minutes, and subsequent experiments were performed according to the manufacturer's instructions.

First Ligation (SelPH-Adaptor)

2.5 µl of 15 µM SelPH-adaptor, NEBNext Ultra II ligation master mix and NEBNext ligation enhancer were added to and mixed well with the reaction mixture, and then ligation was performed according to the manufacturer's instructions.

Post-Ligation Cleanup

A 2× volume of ProNex Chemistry reagent was added to the SelPH-adaptor ligation sample, and the experiment was conducted according to the manufacturer's instructions. 30 µl of elution buffer was added to the mixture, followed by 10 minutes of elution.

First Extension Reaction

4 µl of 10× isothermal amplification buffer, 1 µl of each of 10 mM dNTPs, 0.5 µl of Bst 2.0 DNA polymerase, and 30 µl of the eluted sample were mixed together, and distilled water was added thereto to reach a total volume of 40 µl. Next, the mixture was allowed to react at 60° C. for 10 minutes, and Bst 2.0 DNA polymerase was added thereto, followed by reaction at 65° C. for 5 minutes.

Post-Amplification Cleanup

A 2× volume of ProNex Chemistry reagent was added to the first extension sample, and the mixture was allowed to react according to the manufacturer's instructions. In this case, 40 µl of elution buffer was added to the mixture, followed by 10 minutes of elution.

End Repair and A-Tailing

Illumina's NEBNext Ultra II FS DNA library preparation kit was performed using the NEBNext Ultra end-repair/dA-tailing module (NEB) as an enzyme mixture for performing fragmentation together with end-repair and A-tail. 6.5 µl of 10× end repair reaction buffer and 3 µl of end prep mix were added to 40 µl of the eluted sample, and then the total volume was adjusted to 65 µl with distilled water, and the experiment was conducted according to the manufacturer's instructions.

Second Ligation (NGS Adaptor)

The NGS adaptor contained in NEXTFlex Rapid DNA Sequencing Bundle (Bioo Scientific) was used. 2.5 µl of 25 µM NGS-adaptor was added to the sample subjected to A-tailing, and the reaction was performed according to the manufacturer's instructions.

Post-Ligation Cleanup

A 2× of ProNex Chemistry reagent was added to the sample subjected to NGS-adaptor ligation, and the experiment was conducted according to the manufacturer's instructions, and 40 µl of elution buffer was added to the mixture, followed by 10 minutes of elution.

Second Extension Reaction

4 µl of 10× isothermal amplification buffer, 1 µl of each of 10 mM dNTPs, 0.5 µl of Bst 2.0 DNA polymerase, and 30 µl of the eluted sample were mixed together, and distilled water was added thereto to reach a total volume of 40 µl. 2.5 µl of PCR primer 2 (serving as Illumina P7 primer) according to the oligonucleotide sequence provided by Bioo Scientific was added thereto, and the mixture was allowed to react at 65° C. for 10 minutes, and then Bst 2.0 DNA polymerase was added thereto, followed by reaction at 65° C. for 5 minutes.

Post-Amplification Cleanup

A 1.3× volume of ProNex Chemistry reagent was added to the sample subjected to the second extension reaction, and the mixture was allowed to react according to the manufacturer's instructions. 30 µl of elution buffer was added to the mixture, followed by 10 minutes of elution.

5 Gel Electrophoresis

For PAGE (polyacrylamide gel electrophoresis), 2 µl of Novex TBE-Sample buffer (5×) was added to and mixed well with each sample, and 10 µl of the mixture was dispensed onto 10% TBE gel (Invitrogen) and electrophoresed at 200 V for 35 minutes. After electrophoresis, the gel was well separated, and allowed to react with 5 µl of SYBR gold nucleic acid gel stain (diluted in 100 ml of distilled water) in a mixing block for 15 minutes. For agarose gel electrophoresis, 1.5% and 2% agarose gels were made with 1×TBE buffer, and 10 µl of the sample was added to and mixed with 2 µl of a 6× Purple loading dye, and then 10 µl of the mixture was loaded on the gel and electrophoresed at 100 V for 50 minutes.

REFERENCE EXAMPLE

Overall Experimental Process for the Method for NGS Library Preparation Using the Self-Priming and Replicating Hairpin Adaptor of the Present Invention Hereinafter, the overall experimental process of preparing an NGS library using the self-priming and replicating hairpin adaptor (SelPH-adaptor) provided by the present invention will be described (see FIG. 1).

The method for NGS library preparation according to the present invention is largely composed of: phase I of ligating the SelPH-adaptor provided by the present invention; phase II of ligating an NGS adaptor for sequencing.

Figure 1:
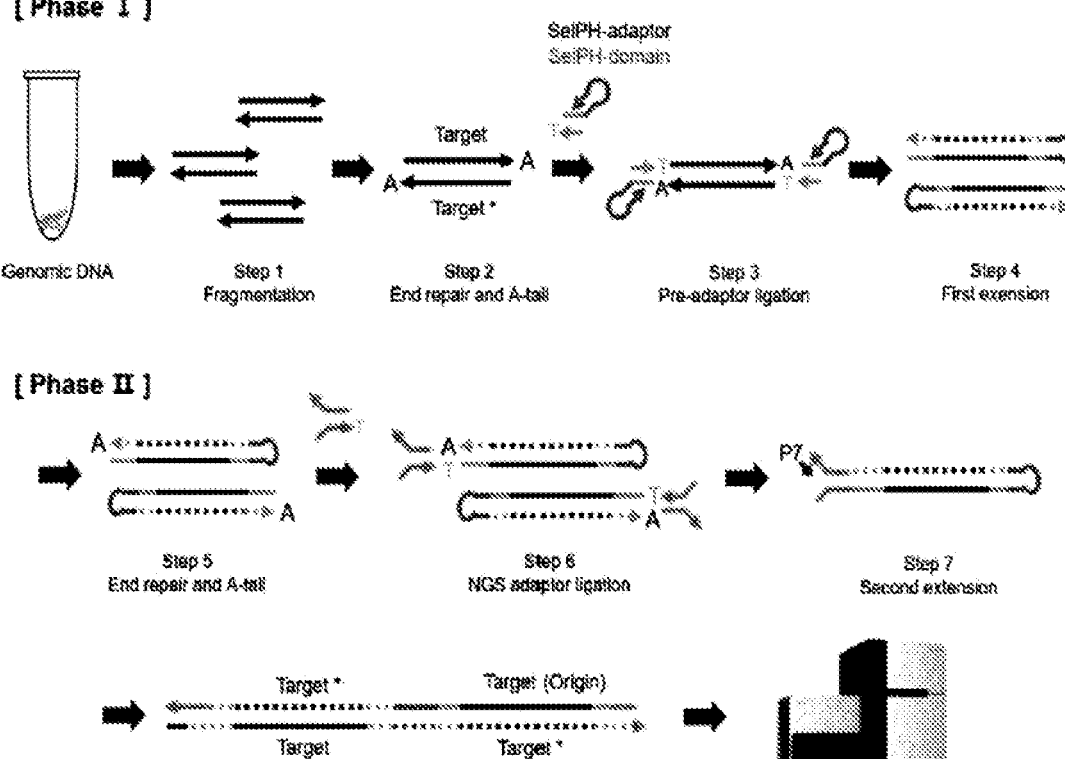
FIG. 1 schematically shows a self-priming and replicating hairpin sequencing (SelPH-seq) process which is a next-generation sequencing method employing the self-priming and replicating hairpin adaptor according to the present invention.

In phase I, in consideration of the length of reads to be sequenced, genomic DNA (gDNA) is fragmented into small fragments (step 1 in FIG. 1), and then end-repair and A-tailing is performed for ligation of SelPH-adaptor (step 2 in FIG. 1). Thereafter, a SelPH-adaptor having a self-priming and replicating domain (SelPH domain) is ligated to the DNA fragment subjected to A-tailing (step 3 in FIG. 1). Then, for self-priming and replicating of the SelPH domain using DNA polymerase, an extension reaction starts from the 3' end through the hybridization stem to the 5' end. As a result, the sense DNA (target) and the antisense DNA (target*) of the DNA fragment are separated from each other to form a long hairpin stem (step 4 in FIG. 1).

Next, phase II is performed, in which end-repair and A-tailing for ligation of an NGS adaptor to the DNA prepared in phase I and having a long hairpin stem shape is performed (step 5 in FIG. 1). Thereafter, the NGS adaptor is ligated, and an extension reaction is performed using a P7 primer and a DNA polymerase having a strand displacement function (step 7 in FIG. 1), and thus the DNA having a long hairpin stem shape is replicated by the polymerase and has an unfolded form. Eventually, a duplex DNA having P5 and P7 at both ends is formed.

Example 1

NGS Analysis Using the Self-Priming and Replicating Hairpin Adaptor of the Present Invention <1-1> Preparation of Self-Priming and Replicating Hairpin Adaptor (SelPH-Adaptor) and Confirmation of Self-Priming and Replication As shown in Table 6 below, the present inventors designed a long single-stranded oligonucleotide including a SelPH-domain, and a short single-stranded oligonucleotide constituting a hybridization stem required for ligation, in order to prepare a SelPH-adaptor. First, the short single strand was T-tailed at the 3' end so that it could be combined with the A-tail by adaptor ligation, and the 5' end thereof was not phosphorylated to prevent ligation with the 3' end of the long single strand. The long single-stranded SelPH-domain should have a structure to which DNA polymerase can bind well, and it should be capable of self-priming and replicating by forming and maintaining a hairpin structure well at the temperature (65° C.) where an extension reaction is performed. Accordingly, in order to prepare a self-priming and replicating adaptor satisfying such optimal conditions, the present inventors added each of SelPH-domain candidate nucleotide sequences having lengths of 8 bp, 10 bp and 12 bp, respectively, to the 3' end of an oligonucleotide having 40 nucleotides (see a of FIG. 2). Then, it was confirmed that extension was achieved using Q5 DNA polymerase, suggesting that self-priming and replication was possible. Meanwhile, among the hairpin stems having different lengths, the 12-bp hairpin stem showed the best stability, and thus the 12-bp hairpin stem was used for preparation of the SelPH-adaptor of the present invention (see b of FIG. 2). In addition, 4 adenines (A) were added between the end of the hybridization stem and the beginning of the SelPH-domain, so that the 3' end of the SelPH-domain and the 5' end of the short single strand were not ligated to each other during adaptor ligation.

TABLE 6

| Primer for conformation of self-priming and replication | Nucleotide sequence (5'→3') |
|---|---|
| SelPH-adaptor (long single strand, containing 8-bp SelPH domain) | GAACT ACTTG GAGGA CCGTC GCTTG GTGCA CCGCG ACCTG CGAC ATCT AAAA AGAT GTCG (SEQ ID NO: 1) |
| SelPH-adaptor (long single strand, containing 10-bp SelPH domain) | GAACT ACTTG GAGGA CCGTC GCTTG GTGCA CCGCG ACCTG GC ACAC ATCT AAAA AGAT GTGT GC (SEQ ID NO: 2) |
| SelPH-adaptor (long single strand, containing 12-bp SelPH domain) | GAACT ACTTG GAGGA CCGTC GCTTG GTGCA CCGCG ACCTG GGGA CGAC ATCT AAAA AGAT GTCG TCGC (SEQ ID NO: 3) |
| SelPH-adaptor (short single strand) | GCTC GCTT ATCCT Bold "T": T-tailed (SEQ ID NO: 5) |

The nucleotide sequence shown in blue in Table 6 corresponds to the nucleotide sequence shown in blue in a of FIG. 2.

<1-2> Preparation of Synthetic DNAs Having Various Lengths

In Order to Confirm that Self-Priming and Replication occurs even when the self-priming and replicating hairpin adaptor (SelPH-adaptor) of the present invention prepared in <1-1> above is ligated to double-stranded DNA, synthetic DNAs for NGS analysis having various lengths were prepared.

Preparation of 91-bp Synthetic DNA

Figure 3:
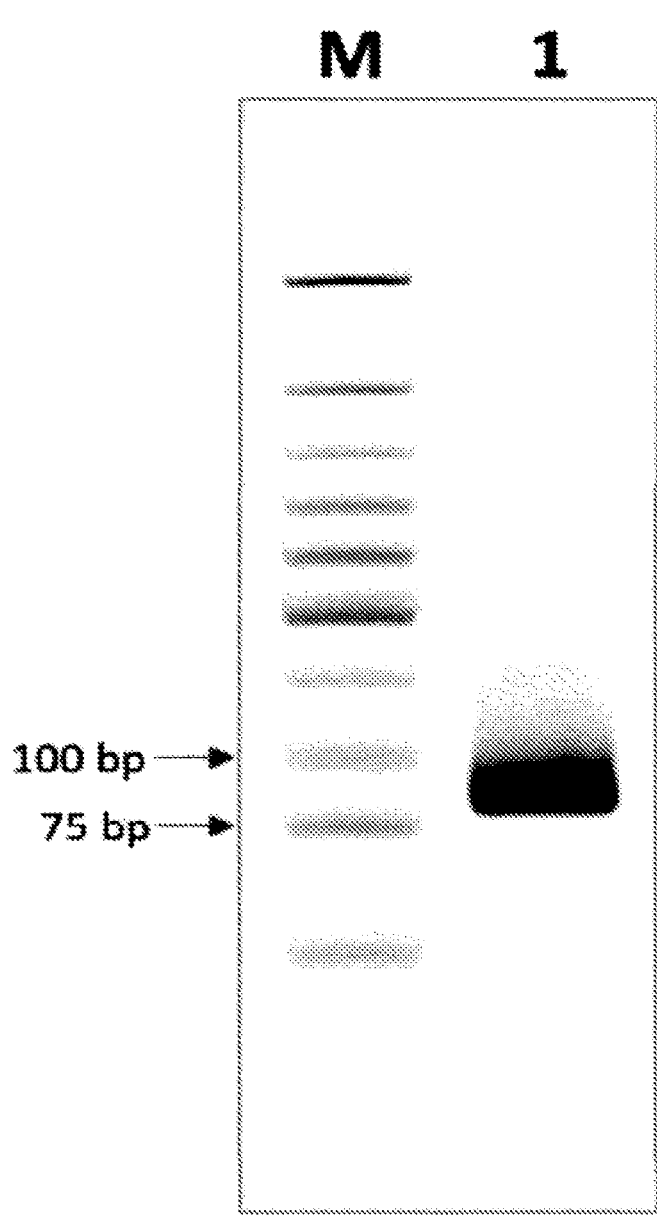
FIG. 3 shows the results of PAGE analysis of a 91-bp synthetic insert DNA extracted from exon 21 of EGFR gene in one example of the present invention.

In order to prepare a 91-bp synthetic DNA as a small insert DNA, the sequence of exon 21 of the EGFR gene was searched in NCBI, a single-stranded DNA having a total length of 91 bases was complementarily synthesized by adding adenine to the 3' end of an oligonucleotide having 90 bases (positions 1 to 90). These single strands were annealed by lowering the temperature slowly from 95° C. to 20° C., thus preparing a double-stranded 91-bp synthetic DNA (see FIG. 3).

Preparation of 285-bp Synthetic DNA

Figure 4:
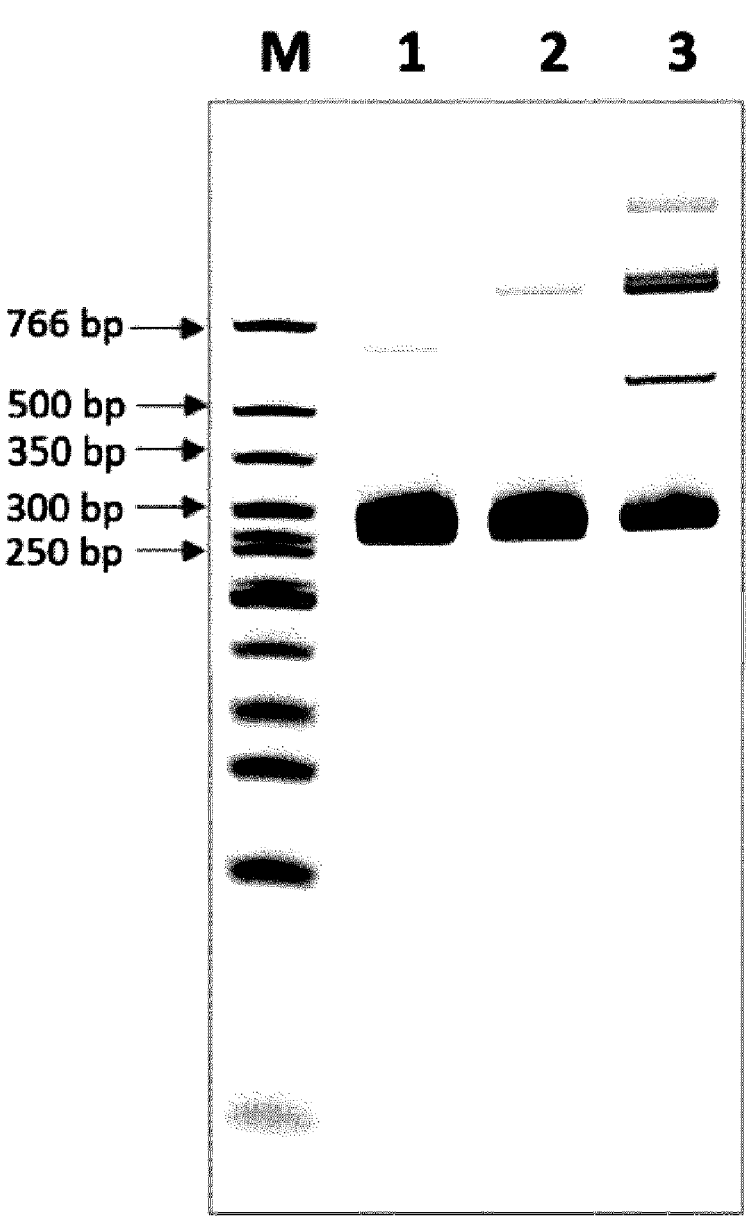
FIG. 4 shows the results of performing PAGE analysis of PCR products with different annealing temperature to obtain a 285-bp synthetic insert DNA, which targets position 1,041 of BRCA1 gene, in one example of the present invention.

Next, for preparation of insert DNA having a longer length than 91 bp, a 285-bp DNA fragment that targets position 1041 of the BRCA1 gene was prepared. Template DNA was subjected to PCR at different temperatures (54° C., 57° C. and 60° C.), and then PCR fragments were analyzed by PAGE gel (see FIG. 4). In this case, nested PCR was performed to obtain a 285-bp single band, and as a result, it was confirmed through PAGE gel that only a band with a size of 285 bp existed (see FIG. 5). The 285-bp nucleotide sequence is shown in SEQ ID NO: 8.

<1-3> Establishment of Ligation Conditions

As described above, the NGS preparation process according to the present invention comprises: phase I in which ligation of the adaptor of the present invention and an extension reaction are performed; and phase II in which ligation of the NGS adaptor and an extension reaction are performed. In phase I, the extension reaction occurs with self-priming and replication of the SelPH domain only when ligation between the SelPH-adaptor of the present invention and the DNA fragment is performed. In addition, only when the extension reaction in phase I is performed, does ligation with the NGS adaptor in phase II become possible. Therefore, the present inventors determined the optimal conditions for ligation with the SelPH-adaptor of the present invention and the extension reaction by using 91-bp and 285-bp insert DNAs.

For establishment of ligation conditions, ligation reaction was performed using four selected products: NEXTFlex Rapid DNA Sequencing Bundle (Bioo Scientific), KAPA HyperPlus Kit (KAPA Biosystems), Illumina's NEBNext Ultra II FS DNA library Prep Kit (NEB), and Blunt/TA Ligase Master Mix (NEB). Here, the mixing ratio between the insert DNA: SelPH-adaptor of the present invention was set to 1:20.

As a result of analyzing the 91-bp insert DNA, the faint band shown at the bottom of a of FIG. 6 was SelPH-adaptor, and the double-stranded portion was 24 bp in total. However, considering that some have a hairpin structure and exist in a partially single-stranded form, a slight difference in movement during electrophoresis can be expected. The band size of the ligated SelPH-adaptor was calculated to be 28 bp.

From the results in a of FIG. 6, it could be seen that, among the bands clustered in the middle, the 91-bp band located at the bottom corresponded to an insert DNA with no SelPH-adaptor ligated at both ends, and the 119-bp band located in the middle corresponded to a DNA with the adaptor ligated only at one end, and the 147-bp band corresponded to a DNA with the adaptor ligated at both ends. In addition, it was confirmed that, among the four products, the use of Bioo Scientific's product was preferred when synthetic insert DNA was used, and the use of NEB's product was preferred when fragmentation was required.

In addition, in order to find the conditions where SelPH-adaptor can be ligated at both ends, ligation was performed at a fixed SelPH-adaptor: DNA concentration ratio of 1:20 while changing the ligation time. As a result, when the ligation time was increased from 15 minutes to 60 minutes and 18 hours, the band pattern was similar between the ligation times (see a of FIG. 7), and when ligation with 285-bp insert DNA was performed for 60 minutes, the band pattern was similar to that of the 91-bp insert DNA (see b of FIG. 7). Meanwhile, it was confirmed that, even if the adaptor was ligated at both ends ligated or ligated at only one end, both self-priming and replication were possible, suggesting that a ligation time of 15 minutes was efficient. Therefore, the ligation in each of phases I and II was performed for 15 minutes.

<1-4> Establishment of Extension Reaction Conditions

Next, in order to establish the conditions for the extension reaction occurring after ligation of the SelPH-adaptor, analysis was made of the results of the extension reaction performed using each of Q5 DNA polymerase, Phi29 DNA polymerase having strand displacement function, and Bst 2.0 DNA polymerase. Here, Q5 DNA polymerase requires a denaturation process at 98° C., and the melting temperature of the hairpin stem is as high as 78° C. If the hairpin structure is not properly formed in the process of raising and lowering the temperature, self-priming and replication may not be possible. For this reason, in the experiment using Q5 DNA polymerase, the temperature after the denaturation process was very slowly lowered to 78° C., which is the melting temperature of the hairpin stem, and 65° C., which is the annealing temperature, so that the hairpin structure could be well formed.

When the extension reaction is performed, if the extension reaction occurs from the band ligated with SelPH-adaptor for the 91-bp insert DNA, the following four band may appear: two double-stranded DNA having a length of 135 bp in the case of the insert DNA having the adaptor ligated at both ends; one double-stranded DNA having a length of 123 bp and one single strand having a length of 103 bp in the case of the insert DNA having the adaptor ligated at only one end; and non-ligated 91-bp insert DNA (see FIG. 8).

As a result of analyzing the results of the extension reaction, it could be seen that, when Q5 DNA polymerase was used, bands at 135 bp and 123 bp were clear, but many other bands were present at the upper end, and when Phi29 DNA polymerase was used, a pattern similar to that of the SelPH-adaptor ligation sample used as a control appeared, suggesting that the extension reaction did not proceed well, and when Bst 2.0 DNA polymerase was used, bands at 135 bp and 123 bp were clear, and bands having different sizes appeared at the upper end. Thus, it could be seen that it is most suitable to use Bst 2.0 DNA polymerase in the extension reaction of the present invention (see a of FIG. 8).

<1-5> Carrying Out of Phase I and Phase II Processes Using SelPH-Adaptor of the Present Invention Using the SelPH-adaptor of the present invention, NGS analysis was performed by performing phase I and phase II processes on 91-bp and 285-bp insert DNAs under optimal conditions for ligation and extension reaction.

For each of 91-bp and 285-bp insert DNAs, the SelPH-adaptor of the present invention and the insert DNA were mixed together at a molar concentration ratio of 1:20, and ligated to each other using NEXTFlex Rapid DNA Sequencing Bundle (Bioo Scientific) for 15 minutes. Thereafter, an extension reaction was performed using Bst 2.0 DNA polymerase, thus completing phase I. Thereafter, the sample subjected to phase I was subjected to end-repair and A-tailing, and then Bioo Scientific's NEXTFlex DNA barcode adaptor, which is an NGS adaptor, was ligated thereto.

In this case, the NGS adaptor is a 12-bp Y-shaped adaptor hybridized with a 58-bp single strand T-tailed with P5, and a 63-bp single-stranded DNA including P7' and index. When the 91-bp insert DNA is used, four bands (135 bp, 123 bp, 103 bp, and 91 bp) may appear during the first extension. Here, if the NGS adaptor is calculated to be approximately 60 bp in length, the four bands correspond to 195 bp, 183 bp, 163 bp, and 152 bp, respectively, and unligated insert DNA may also exist.

In the actual analysis results, two bands appeared around 60 bp in lane 4 in FIG. 9, which indicates that the NGS adaptor was separated in the electrophoresis process and appeared as single strands. Two thick bands corresponding to extension reaction products appeared in lane 3, and these bands are believed to be the first extension reaction products remaining due to non-ligation of the NGS adaptor. It can be seen that the dark band at the top corresponds to the insert DNA properly ligated with the NGS adaptor. Lane 5 shows the second extension reaction products after ligation of the NGS adaptor, and the two dark bands in lane 5 correspond to products produced because the phase I products resulting from the extension reaction after ligation of the SelPH-adaptor were subjected to the extension reaction with P7 primer and Bst 2.0 DNA polymerase, the sizes of these bands were 389 bp and 365 bp, which were approximately doubled.

In addition, when the 285-bp insert DNA was used, four bands (329 bp, 317 bp, 297 bp and 285 bp) appeared, which correspond to 389 bp, 377 bp, 357 bp and 345 bp, respectively, when the NGS adaptor is calculated to be about 60 bp in length. As a result of performing phase I and II processes on the 285 bp insert DNA, as shown in shown in FIG. 10, the amplification product having the expected size could be obtained.

Therefore, from these results, the present inventors could see that sequencing using the SelPH-adaptor designed in the present invention could work well, and that it was possible to prepare an NGS library using the SelPH-adaptor.

Example 2

NGS Analysis on Yeast Genome Using Self-Priming and Replicating Hairpin Adaptor of the Present Invention As it was confirmed through Example 1 that NGS analysis on the synthetically prepared insert DNAs using the SelPH-adaptor of the present invention was well performed, the present inventors conducted the following experiment to confirm whether the adaptor of the present invention would work well even on actual genomic DNA.

<2-1> Library Preparation

In order to fragment *Saccharomyces cerevisiae* (By4741), a yeast genome having a size of about 12 Mb, Illumina's NEXTFlex Ultra II FS DNA Library Prep kit (NEB) was used, and the size of the insert DNA of the yeast genome was set to 100-150 bp.

<2-2> Confirmation of Library Preparation

The reactions of phases I and II were performed on the insert DNA of the yeast genome prepared in <2-1> under the same conditions as in <1-5> of Example 1, and the reaction products were analyzed.

As a result, as shown in FIG. 12, it could be confirmed that, when the 100 to 150-bp insert DNA was used, the desired duplicate product of 380-500 bp in length was produced after completion of the extension reaction of phase II.

From the above results, the present inventors could confirm that, when the SelPH-adaptor devised in the present invention is used, it is possible to reduce biased amplification which results from several rounds of PCR required in the prior art, because one extension reaction is performed through the self-priming and replicating function of the SelPH domain; errors caused by not using high-fidelity DNA polymerase and errors caused by the error rate of DNA polymerase itself may be corrected because a duplicate product is produced in the analysis using the SelPH-adaptor of the present invention; it is possible to prepare a library with a lower error rate and higher efficiency than a conventional method, because there is no error that may occur due to DNA damage and there is no restriction on the length of the DNA fragment, unlike the conventional circular DNA-based method; and it is possible to more accurately detect even mutant sequences present at low frequencies.

So far, the present invention has been described with reference to the embodiments. Those skilled in the art will appreciate that the present invention can be implemented in modified forms without departing from the essential features of the present invention. Therefore, the disclosed embodiments should be considered in descriptive sense only and not for purposes of limitation. Therefore, the scope of the present invention is defined not by the detailed description of the present invention but by the appended claims, and all modifications within a range equivalent to the scope of the appended claims should be construed as being included in the present invention.

The invention claimed is:

1. A self-priming and replicating hairpin adaptor for next-generation sequencing (NGS) library preparation comprising: a long single-stranded first oligonucleotide consisting of the nucleotide sequence of SEQ ID NO: 4 and having a hairpin structure; and a short single-stranded second oligonucleotide consisting of the nucleotide sequence of SEQ ID NO: 5.

2. The self-priming and replicating hairpin adaptor of claim 1, wherein polymerase binds to the first oligonucleotide, and the hairpin structure is maintained even during an extension reaction.

3. The self-priming and replicating hairpin adaptor of claim 1, wherein the 5' end of the second oligonucleotide consisting of the nucleotide sequence of SEQ ID NO: 5 is not phosphorylated so as not to be ligated to the 3' end of the first oligonucleotide.

4. A method for next-generation sequencing (NGS) preparation comprising steps of:
   (1) fragmenting genomic DNA to be analyzed;
   (2) ligating the self-priming and replicating hairpin adaptor of claim 1 to an end of the fragmented genomic DNA to be analyzed;
   (3) adding polymerase to a reaction solution containing the fragmented genomic DNA to which the self-priming and replicating hairpin adaptor has been ligated in step (2), followed by an extension reaction to obtain a first reaction product;

(4) ligating a universal adaptor for NGS to the first reaction product;
   (5) adding polymerase to a reaction solution containing the first reaction product to which the universal adaptor for NGS has been ligated in step (4), followed by an extension reaction to obtain a second reaction product; and
   (6) purifying the second reaction product.

5. The method of claim 4, wherein the fragmented genomic DNA to be analyzed and the self-priming and replicating hairpin adaptor, which are used in step (2), are mixed with each other at a molar ratio of 1 (genomic DNA):15 (adaptor) to 1:25.

6. The method of claim 4, further comprising, before ligating the self-priming and replicating hairpin adaptor in step (2) and before ligating the universal adaptor for NGS in step (4), a step of adding adenosine to the 3' end of the DNA (A-tailing) after end repair of the DNA.

7. The method of claim 4, wherein the first reaction product in step (4) is an amplification product comprising the nucleotide sequence of the self-priming and replicating hairpin adaptor and having an extended hairpin structure.

8. The method of claim 4, wherein the second reaction product in step (5) is in the form of linear duplex DNA formed by amplification in the extension reaction.

9. The method of claim 4, wherein each of the extension reaction in step (3) and the extension reaction in step (5) is performed once.

10. A kit for DNA library preparation comprising the self-priming and replicating hairpin adaptor for next-generation sequencing (NGS) library preparation according to claim 1.

\* \* \* \* \*

SEQUENCE LISTING

```
<160> NUMBER OF SEQ ID NOS: 11

<210> SEQ ID NO 1
<211> LENGTH: 60
<212> TYPE: DNA
<213> ORGANISM: Artificial Sequence
<220> FEATURE:
<223> OTHER INFORMATION: 8bp adaptor sequence

<400> SEQUENCE: 1
gaactacttg gaggaccgtc gcttggtgca ccgcgacctg cgacatctaa aaagatgtcg      60

<210> SEQ ID NO 2
<211> LENGTH: 64
<212> TYPE: DNA
<213> ORGANISM: Artificial Sequence
<220> FEATURE:
<223> OTHER INFORMATION: 10bp adaptor sequence

<400> SEQUENCE: 2
gaactacttg gaggaccgtc gcttggtgca ccgcgacctg gcacacatct aaaaagatgt      60
cggc                                                                  64
```

```
<210> SEQ ID NO 3
<211> LENGTH: 68
<212> TYPE: DNA
<213> ORGANISM: Artificial Sequence
<220> FEATURE:
<223> OTHER INFORMATION: 12bp adaptor sequence

<400> SEQUENCE: 3
gaactacttg gaggaccgtc gcttggtgca ccgcgacctg gcgacgacat ctaaaaagat      60
gtcgtcgc                                                               68

<210> SEQ ID NO 4
<211> LENGTH: 44
<212> TYPE: DNA
<213> ORGANISM: Artificial Sequence
<220> FEATURE:
<223> OTHER INFORMATION: SelPH adaptor long strand sequence

<400> SEQUENCE: 4
ggataaggga gcaaaagcga cgacatctaa aaagatgtcg tcgc                       44

<210> SEQ ID NO 5
<211> LENGTH: 12
<212> TYPE: DNA
<213> ORGANISM: Artificial Sequence
<220> FEATURE:
<223> OTHER INFORMATION: SelPH adaptor short strand sequence

<400> SEQUENCE: 5
gctcccttat cc                                                          12

<210> SEQ ID NO 6
<211> LENGTH: 91
<212> TYPE: DNA
<213> ORGANISM: Artificial Sequence
<220> FEATURE:
<223> OTHER INFORMATION: 91bp insert DNA sequence

<400> SEQUENCE: 6
ggcatgaact acttggagga ccgtcgcttg gtgcaccgcg acctggcagc caggaacgta      60
ctggtgaaaa caccgcagca tgtcaagatc a                                     91

<210> SEQ ID NO 7
<211> LENGTH: 91
<212> TYPE: DNA
<213> ORGANISM: Artificial Sequence
<220> FEATURE:
<223> OTHER INFORMATION: 91bp insert DNA sequence(complementary DNA of
      seq ID number 7)

<400> SEQUENCE: 7
gatcttgaca tgctgcggtg ttttcaccag tacgttcctg ctgccaggt cgcggtgcac       60 caagcgacgg tcctccaagt agttcatgcc a                                     91

<210> SEQ ID NO 8
<211> LENGTH: 285
<212> TYPE: DNA
<213> ORGANISM: Artificial Sequence
<220> FEATURE:
<223> OTHER INFORMATION: 285bp insert DNA sequence

<400> SEQUENCE: 8
ctgaattctg taataaaagc aaacagcctg gcttagcaag gagccaacat aacagatggg      60
```

-continued

```
ctggaagtaa ggaaacatgt aatgataggc ggactcccag cacagaaaaa aaggtagatc      120
tgaatgctga tcccctgtgt gagagaaaag aatggaataa gcagaaactg ccatgctcag      180
agaatcctag agatactgaa gatgttcctt ggataacact aaatagcagc attcagaaag      240
ttaatgagtg gttttccaga agtgatgaac tgttaggttc tgatg                      285
```

```
<210> SEQ ID NO 9
<211> LENGTH: 24
<212> TYPE: DNA
<213> ORGANISM: Artificial Sequence
<220> FEATURE:
<223> OTHER INFORMATION: Illuminas P7 primer

<400> SEQUENCE: 9
caagcagaag acggcatacg agat                                             24
```

```
<210> SEQ ID NO 10
<211> LENGTH: 20
<212> TYPE: DNA
<213> ORGANISM: Artificial Sequence
<220> FEATURE:
<223> OTHER INFORMATION: BRCA1 gene position 1041 primer forward

<400> SEQUENCE: 10
ctgaattctg taataaaagc                                                  20
```

```
<210> SEQ ID NO 11
<211> LENGTH: 20
<212> TYPE: DNA
<213> ORGANISM: Artificial Sequence
<220> FEATURE:
<223> OTHER INFORMATION: BRCA1 gene position 1041 primer reverse

<400> SEQUENCE: 11
catcagaacc taacagttca                                                  20
```